United States Patent [19]
Pollard et al.

[11] Patent Number: 6,083,954
[45] Date of Patent: Jul. 4, 2000

[54] METHOD OF TREATING CYSTIC FIBROSIS

[76] Inventors: Harvey B. Pollard, 11008 Lamplighter La., Potomac, Md. 20854; Kenneth A. Jacobson, 11606 Fulham St., Silver Spring, Md. 20903

[21] Appl. No.: 09/114,537

[22] Filed: Jul. 13, 1998

Related U.S. Application Data

[60] Division of application No. 08/343,714, Nov. 22, 1994, Pat. No. 5,877,179, which is a continuation-in-part of application No. 07/952,965, Sep. 29, 1992, Pat. No. 5,366,977.

[51] Int. Cl.$^7$ ......................... A61K 31/52; C07D 473/06
[52] U.S. Cl. ......................... 514/263; 514/267; 514/273; 544/273
[58] Field of Search ................... 514/263, 273, 514/267; 544/273

[56] References Cited

U.S. PATENT DOCUMENTS

| | | | |
|---|---|---|---|
| 4,548,818 | 10/1985 | Kjellin et al. ............................ | 514/263 |
| 4,593,095 | 6/1986 | Snyder .................................... | 544/272 |
| 4,772,607 | 9/1988 | Badger .................................... | 514/263 |
| 4,866,072 | 9/1989 | Edwards et al. ......................... | 514/291 |
| 5,032,593 | 7/1991 | Rzeszotarski et al. .................. | 514/263 |
| 5,096,916 | 3/1992 | Skupin .................................... | 514/401 |
| 5,366,977 | 11/1994 | Pollard et al. ........................... | 514/263 |

FOREIGN PATENT DOCUMENTS

| | | |
|---|---|---|
| 0 374 808 | 6/1990 | European Pat. Off. . |
| 94/03456 | 2/1994 | WIPO . |
| 94/25605 | 11/1994 | WIPO . |
| 94/25607 | 11/1994 | WIPO . |

OTHER PUBLICATIONS

Arispe et al., *Proc. Natl. Acad. Sci. USA*, 89, 1539–1543 (1992).
Bradlett et al., *biochem. Pharm.*, 39 1897 (1990).
Cheng et al., *Biochem. Pharmacol.*, 22, 3099–3108 (1973).
Daly et al., *J. Med. Chem.*, 29, 1305–1308(1986).
Edwards,*Neuroscience*, 7, 1335–1366(1982).
Eidelman et al., *Proc. Natl. Acad. Sci USA*, 89, 5562–5566(1992).
Hide et al., *Mol. Pharmcol.*, 41, 352–359(1992).
Jacobson et al., *Biochemistry*, 34, (28), 9088–9094 (1995).
Jacobson et al.,*J. Med. Chem.*, 36, 1333–1342(1993).
Jacobson et al., *J. Med. Chem.*, 36, 2639–2644(1993).
Jacobson et al.,*Biochem. Pharmacol.*, 37, 3653–3661(1988).
Jarvis et al.,*J. Pharmacol. Exp. Therapeut.*, 251, 888–893 (1989).
Knowles et al.,*N. E. J. Med.*, 325, 533–538(1991).
Knowles et al.,*N. E. J. Med.*, 322, 1189–1194(1990).
Müller et al.,*J. Med. Chem.*, 36, 3341–3349(1993).
Riordan et al.,*Science*, 245, 1066–1073(1989).
Schoumacher et al.,*Proc. Natl. Acad. Sci. USA*, 87, 4012–4016(1990).
Schwabe et al.,*Naunyn Schmiedeberg's Arch. Pharmacol.*, 313, 179–187(1980).
Shamim et al.,*J. Med. Chem.*, 32, 1231–1237(1989).
Shamim et al.,*J. Med. Chem.*, 31, 613 (1988).
Shimada et al.,*J. Med. Chem.*, 35, 924–930(1992).
Thomas et al.,*Science*, 251, 555–557 (1991).
Thompson et al.,*J. Med. Chem.*, 34, 2877–2882(1991).
Ukena et al.,*FEBS*, 209, 122–128(1986).
van Galen et al.,*Med. Res. Rev.*, 12, 423–471 (1992).
Ward et al.,*J. Gen. Physiol.*, 104, 33a(1994).

*Primary Examiner*—Bennett Celsa
*Attorney, Agent, or Firm*—Leydig, Voit & Mayer

[57] ABSTRACT

The present invention provides a method of identifying CFTR-binding compounds for treating cells having a reduced apical Cl$^-$ conductance, such as cystic fibrosis cells. This identification method involves the use of polypeptide I$\alpha$, which constitutes a portion of the CFTR protein. The present invention also provides a method of treating CF cells by contacting cells having a reduced apical Cl$^-$ conductance with a therapeutically effective quantity of a compound selected by the present inventive identification method. Preferred compounds for such treatment have little or no affinity for adenosine cell receptors. The present invention provides novel compounds useful in practicing the present inventive method, as well as pharmaceutical compositions containing such compounds.

11 Claims, 11 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 32 amino acids
      (B) TYPE: amino acid
      (C) STRANDEDNESS: single
      (D) TOPOLOGY: linear (ii) MOLECULE TYPE: polypeptide (xi) SEQUENCE DESCRIPTION: SEQ ID NO:1:

```
Pro Ser Glu Gly Lys Ile Lys His Ser Gly Arg Ile Ser Phe Cys Ser
1               5                  10                  15

Gln Phe Ser Trp Ile Met Pro Gly Thr Ile Lys Glu Asn Glu Glu Phe
            20                  25                  30
```

(2) INFORMATION FOR SEQ ID NO:2:

(i) SEQUENCE CHARACTERISTICS:
      (A) LENGTH: 96 base pairs
      (B) TYPE: nucleic acid (C) STRANDEDNESS: single
        (D) TOPOLOGY: linear (ii) MOLECULE TYPE: mRNA (xi) SEQUENCE DESCRIPTION: SEQ ID NO:2:

CCNUCNGARG GNAARAUHAA RCAYUCNGGN CGNAUHUCNU UYUGYUCNCA RUUYUCNUGG        60

AUHAUGCCNG GNACNAUHAA RGARAAYGAR GARUUY        96

(2) INFORMATION FOR SEQ ID NO:3:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:3:

Gly Val Ser Tyr Asp Glu Tyr Arg Tyr Arg Ser Val Ile Lys Ala Cys
1               5                   10                  15

Gln Leu Glu Glu Asp Ile Ser Lys Phe Ala Glu Lys Asp Asn Ile
            20                  25                  30

(2) INFORMATION FOR SEQ ID NO:4:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:4:

Gly Thr Ile Lys Glu Asn Glu Glu Phe Gly Val Ser Tyr Asp Glu Tyr
1               5                   10                  15

Arg Tyr Arg Ser Val Ile Lys Ala Cys Gln Leu Glu Glu Asp Ile Ser
            20                  25                  30

(2) INFORMATION FOR SEQ ID NO:5:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:5:

GGNGUNUCNU AYGAYGARUA YCGNUAYCGN UCNGUNAUHA ARGCNUGYCA RUURGARGAR        60

GAYAUHUCNA ARUUYGCNGA RAARGAYAAY AUH        93

(2) INFORMATION FOR SEQ ID NO:6:

(i) SEQUENCE CHARACTERISTICS:
        (A) LENGTH: 96 base pairs
        (B) TYPE: nucleic acid
        (C) STRANDEDNESS: single
        (D) TOPOLOGY: linear -continued (ii) MOLECULE TYPE: mRNA (xi) SEQUENCE DESCRIPTION: SEQ ID NO:6:

GGNACNAUHA ARGARAAYGA RGARUUYGGN GUNUCNUAYG AYGARUAYCG NUAYCGNUCN    60

GUNAUHAARG CNUGYCARUU RGARGARGAY AUHUCN    96

METHOD OF TREATING CYSTIC FIBROSIS

CROSS-REFERENCE TO RELATED APPLICATION

This is a divisional of U.S. patent application Ser. No. 08/343,714, filed Nov. 22, 1994, now U.S. Pat. No. 5,877,179 which is a CIP of 07/952,965, filed Sep. 29, 1992, now U.S. Pat. No. 5,366,977.

FIELD OF THE INVENTION

The present invention relates to a method of identifying CFTR-binding compounds for treating cells having a reduced apical Cl⁻ conductance, such as cystic fibrosis cells. The present invention further relates to compounds and pharmaceutical compositions thereof useful in treating such cells.

BACKGROUND OF THE INVENTION

Healthy animal cells require, among other conditions and materials, the movement of various inorganic ions across the cell membrane to be maintained such that a proper balance of the ions provide the requisite electrical potential across the cellular membrane as well as a life-promoting internal ionic strength. For example, $Na^+$, $Cl^-$, $K^+$, and $Ca^{++}$ are known to cross cell membranes in animals such that $K^+$ and $Ca^{++}$ are accumulated intracellularly to a varying extent in different cells at different times of development, whereas $Na^+$, in large measure, is excluded from the interior of a cell. The cross-cellular movement of these ions is mediated by $Na^+/K^+$- and $Ca^{++}$-dependent ATPases that are membrane bound at the sites of appropriate ion channels. Chloride ion was believed to permeate animal cells by passive means to equilibrate in concentration between the external and internal fluid, resulting in an underrepresentation of $Cl^-$ intracellularly in consequence of the overall negative intracellular change. Conductance of chloride, however, has been shown to be mediated actively as well, by means of a $Cl^-$ channel (see Edwards, *Neuroscience*, 7, 1335–1366 (1982)).

Results from research directed to the pathology of cystic fibrosis ("CF") has provided information on the ill-effects that an ion conductance impairment at the cellular level can have on a person's health, at many levels. CF was known to have a genetic basis because of its differential incidence among white Americans (between 1/1600 and 1/2000 live births) as compared to African Americans (about 1/17,000 live births). Indeed, research over the past decade has revealed that a heritable discrete gene mutation is associated with the clinical symptoms of CF, including abnormal exocrine gland and lung functions.

More specifically, CF is caused by mutations in the cystic fibrosis transmembrane regulator (CFTR) gene, the most common of which is the deletion of a phenylalanine residue at position 508 ($Phe^{508}$; see FIG. 1 for a physical map of the CFTR protein). The mutated CFTR protein is referred to as ΔF508, the site of which is within the first nucleotide binding fold (NBF-1). Schoumacher et al., *Proc. Natl. Acad. Sci.*, 87, 4012–4016 (1990); Riordan et al., *Science*, 245, 1066–1073 (1979). More specifically, this mutation is located in a lengthy internal segment of the NBF-1, flanked on the N-terminal side by the Walker A sequence (amino acid position 458–471; also referred to as "CFTR[458–471]") and on the C-terminal side by the contiguous C domain (amino acid position 548–560; also referred to as "CFTR[548–560]") and the Walker B domain (amino acid position 561–573; also referred to as "CFTR [561–573]"). The physiological role of the intervening sequence located between CFTR[471] and CFTR[561], which includes the polypeptide sequences of Iα, Iβ, and Io (see FIG. 1), is unknown.

Certain mutations in the CFTR gene, such as that resulting in ΔF508, cause an abnormal potential difference across CF epithelia. The abnormality is due to a reduced cellular apical chloride ($Cl^-$) conductance. Consequently, chloride and sodium transport across epithelial membranes of an individual afflicted with CF, for example, is abnormal. It is also known that cells carrying the ΔF508 mutation have higher than normal CFTR protein bound to their endoplasmic reticulum (hereinafter, "ER"), although wild type cells also retain and degrade a substantial amount of CFTR protein in their ER, albeit much less so than the ΔF508 mutant. Ward et al., *J. Gen. Physiol.*, 104, 33a (1994).

This CFTR mutation apparently is responsible for pathophysiological changes in the respiratory system, among others. Nearly all patients suffering from the disease develop chronic progressive disease of the respiratory system. In the majority of cases, pancreatic dysfunction occurs, and hepatobiliary and genitourinary diseases are also frequent.

Although survival of cystic fibrosis patients has improved in recent years, the median survival is still only about 28 years despite the development and implementation of intensive supportive and prophylactic treatment. Present efforts to combat the disease have focused on drugs that are capable of either activating the mutant CFTR gene product or otherwise causing additional secretion of $Cl^-$ from affected cells. Gene therapy is another area of active research, wherein the anion conductance deficit may be repaired by the introduction of a recombinant wild-type CFTR gene, i.e., a CFTR gene that lacks a mutation that results in the abnormality.

Encouraging clinical results have been reported recently for the use of aerosols containing either amiloride (Knowles et al., *N. Engl. J. Med.*, 322, 1189–1194 (1990)) or a mixture of ATP and UTP (Knowles et al., *N. Engl. J. Med.*, 325, 533–538 (1991)), which slow the accumulation of $Cl^-$ in the epithelium of the trachea.

Other drugs that purportedly are useful in the treatment of CF have been described. For example, U.S. Pat. No. 4,866,072 describes the use of 9-ethyl-6,9-dihydro-4,6-dioxo-10-propyl-4H-pyrano(3,2-g)quinoline-2,8-dicarboxylic acid or a pharmaceutically acceptable derivative thereof in the treatment of CF. U.S. Pat. No. 4,548,818 describes the use of a 3-alkylxanthine to treat chronic obstructive pulmonary disease (COPD). U.S. Pat. No. 5,032,593 describes the use of a 1,3-alkyl substituted 8-phenylxanthine or a pharmaceutically acceptable salt thereof in the treatment of bronchoconstriction. U.S. Pat. No. 5,096,916 describes the use of an imidazoline α-adrenergic blocking agent and vasodilator, such as tolazoline, in the treatment of COPD, including cystic fibrosis, chronic bronchitis and emphysema, or COPD in association with asthma.

Historically, theophylline has been administered to asthmatic and CF patients to enhance lung function. Such lung function enhancement is caused principally by bronchodilation, which is due to the action of theophylline on smooth muscles and inflammation. Theophylline has been shown not only to inhibit phosphodiesterase, but also to antagonize adenosine receptors. Accordingly, because theophylline acts at more than one site, it obviously lacks specificity, thus reducing its usefulness to treat CF. In view of the fact that antagonism of the $A_1$ adenosine receptor, not inhibition of phosphodiesterase, has been shown to result in stimulating chloride efflux from CF cells, such lack of specificity could result in undesired side effects, such as detrimental effects to cardiac, renal, and/or central nervous system tissue. In addition, large doses of theophylline must be administered to achieve a beneficial effect, thus increasing the risk of side effects from the high toxicity of the compound.

Other compounds that resemble theophylline in basic structure have been tested but have not been found to be useful in evoking chloride efflux from CF cells and, therefore, has no or little potential in the treatment of cystic fibrosis. For example, 3-isobutylmethyl xanthine (IBMX), which is structurally similar to theophylline, is nonspecific in activity and highly toxic and, therefore, lacks utility in the treatment of CF. Also ineffective in the activation of chloride efflux are the compounds 2-thio-8-cyclopentyl-1,3-dipropylxanthine (2-thio-CPX), 1,3-dipropyl-8-noradamantylxanthine (KW-3902), and 1,3-dimethyl-8-cyclopentylxanthine (CPT) (see U.S. Pat. 5,366,977). Similarly, substitution of the propyl group at position 1 or 3 of CPX (1,3-dipropyl-8-cyclopentylxanthine) with a one-carbon group generates a compound that is ineffective in activating chloride efflux from CF cells. Clearly, minor structural differences have a significant, if not substantial, impact on the effectiveness of a given compound in the treatment of CF. Accordingly, it will be particularly useful if a method were available for screening compounds for an ability to promote chloride ion conductance in affected cells, which, in turn, would be a candidate therapeutic agent for treatment of cystic fibrosis patients.

The '977 patent, cited above, and Eidelman et al., *Proc. Natl. Acad. Sci. USA*, 89, 5562–5566 (1992), disclosed that CPX is a potent $A_1$ adenosine antagonist that promotes chloride efflux from a human epithelial cell line (CFPAC-1). The CFPAC-1 line, further described in Example 6, expresses the aforementioned CFTR ΔF508 mutation and can be viewed as a first generation screening material for CF-active compounds. Although CPX and its related xanthine amino congeners disclosed in the '977 patent have been shown to be relatively non-toxic and therefore potentially useful for CF treatment, the fact that such compounds have an antagonistic effect on $A_1$-adenosine receptors indicates that such treatment probably will have an additional impact on an animal that is unrelated to the CF affliction. Accordingly, use of such compounds, indeed any compound known to have multiple targets of activity, preferably is avoided because the use of such compounds is, at least, potentially detrimental.

A drug of high potency, low toxicity, and little or no specificity for adenosine receptors, thus, would be a highly desirable and promising therapeutic agent for the treatment of cells having a reduced apical Cl⁻ conductance, such as cystic fibrosis cells. Such a drug would not only find utility in the treatment of cystic fibrosis rer se but would be therapeutically useful in the treatment of COPD in general.

It is an object of the present invention to provide a method for identifying compounds that can activate an impaired chloride conductance channel. It is also an object of the present invention to provide a method of correcting the reduced Cl⁻ conductance of cells that are impaired in such conductance. It is another object of the present invention to provide a method of treating cystic fibrosis cells. It is yet another object of the present invention to provide a method of treating cystic fibrosis cells having a deletion involving phenylalanine at amino acid position 508 of the cystic fibrosis transmembrane regulator. It is also an object of the present invention to provide compounds useful in such methods, in particular novel xanthine derivatives that have little or no affinity for the adenosine receptors but have an ability nonetheless to ameliorate the Cl⁻ imbalance of CF cells by stimulating Cl⁻ efflux.

These and other objects and advantages of the present invention, as well as additional inventive features, will be apparent from the description of the invention provided herein.

BRIEF SUMMARY OF THE INVENTION

The present invention provides certain CFTR polypeptides, such as Iα [SEQ ID NO:1], that exhibit an ability to bind specifically to compounds that are known to activate the CFTR-linked chloride ion efflux in ΔF508 mutant cells and not to bind to compounds that are known not to have such a capability to activate CFTR-linked chloride ion efflux. Moreover, the present invention provides a method for the identification of further compounds capable of activating the CFTR-linked chloride ion efflux. Such a method includes the application of the aforementioned CFTR polypeptides as selective binding agents for ion efflux activating compounds. As a further refinement of the identification method, other CFTR polypeptides, such as Iβ [SEQ ID NO:3] or Io [SEQ ID NO:4], having amino acid sequences of adjacent or overlapping regions of the location of Iα, are also disclosed that, despite their close or overlapping proximity to Iα, have a neutral or negative affinity for compounds known to activate ion efflux.

Application of the aforementioned identification method may be used to identify compounds that have an ability to activate ion efflux in ion efflux deficient cells, such as CF cells, especially those having the ΔF508 mutation. Moreover, such compounds, in the context of the present invention, may be further screened to have little or no affinity for either the $A_1$-adenosine cell receptor or the $A_2$-adenosine cell receptor. Such compounds, accordingly, may be used in a method of treating cells having a reduced apical Cl⁻ conductance, such as cystic fibrosis cells. Specifically, the present inventive method involves contacting cells having a reduced apical Cl⁻ conductance with a therapeutically effective quantity of a compound that has little or no affinity for the $A_1$-, $A_2$-, or $A_3$-adenosine cell receptor. Nevertheless, contact between the inventive compounds and CF cells results in Cl⁻ efflux from such cells.

In particular, the method involves contacting such cells with a compound having the formula:

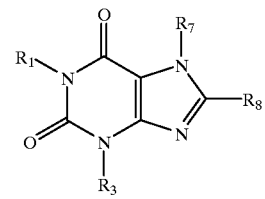

wherein $R_1$ and $R_3$ are the same and are $C_1$–$C_6$ alkyl or $C_1$–$C_6$ alkenyl, $R_7$ is $C_1$–$C_6$ alkyl or hydrogen, and $R_8$ is $C_4$–$C_8$ cycloalkyl. Such a compound may further be selected from the group consisting of 1,3-dipropyl-7-methyl-8-cyclopentylxanthine, 1,3-dipropyl-7-methyl-8-cylcohexylxanthine, cyclohexyl caffeine, 1,3-diallyl-8-cyclohexylxanthine, and therapeutically effective derivatives thereof.

The compounds used in the present inventive method resemble theophylline in basic structure; however, they differ significantly in the substituents at the $R_1$, $R_3$, and $R_8$ positions. Given that minor structural differences in compounds that resemble theophylline have been shown, to render the compounds ineffective or otherwise not useful in the treatment of CF, it was surprising to discover that the aforementioned compounds are effective in activating chloride efflux from CF cells. This discovery was particularly unexpected inasmuch as the apparent mode of activity of the inventive compounds does not involve any of the adenosine receptors.

DETAILED DESCRIPTION OF THE PREFERRED EMBODIMENTS

Figure 1:
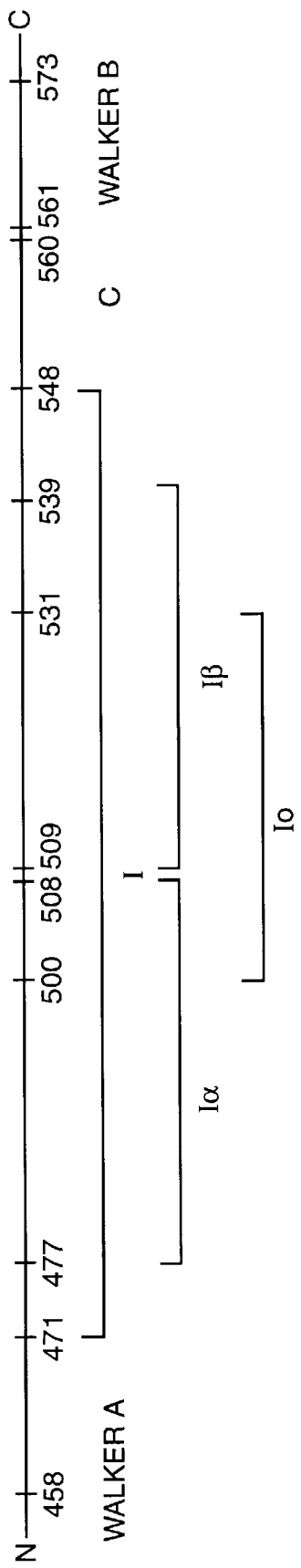
FIG. 1 is a physical map of a portion of the CFTR protein, displaying the location of the following sequences: Walker A (amino acids 458 to 471); Iα (amino acids 477 to 508); Iβ (amino acids 509 to 539); Io (amino acids 500 to 531); C (amino acids 548 to 560); and Walker B (amino acids 561 to 573).

The present invention provides polypeptides that have a positive affinity for compounds that activate chloride ion efflux in CFTR-mutated cells. The polypeptides of the present invention are either a portion of the CFTR protein, namely the segment identified in FIG. 1 as Iα, or a variant thereof having no significant difference in its functioning, as disclosed herein. Iα is defined as the polypeptide that spans from amino acid position 477 to amino acid position 508, and has the following sequence:

NH<sub>2</sub>-PSEGKIKHSGRISFCSQFSWIMPGTIKENE[SEQ ID NO:1]

wherein the capital letters between the NH<sub>2</sub> and COOH groups are the conventional single letter symbols for various amino acids, which protein-related nomenclature is used hereinbelow for SEQ ID NO:3 and SEQ ID NO:4 as well.

Polypeptide Iα [SEQ ID NO:1] may be prepared by (1) analytical or preparative polypeptide synthesis using methods well-known in the art (see, e.g., Atherton et al., *Solid Phase Polypeptide Synthesis, A Practical Approach* (Oxford Univ. Press, 1989)), (2) by appropriate incubation of a microorganism containing a suitable sequence of DNA or RNA for expression of polypeptide Iα using methods of genetic engineering that are well-known in the art (see, e.g., Sambrook et al., *Molecular Cloning: A Laboratory Manual,* (2d ed. 1989)), or (3) by any other suitable means. It is contemplated within the context of the present invention that conservative amino acid changes that, as understood within the art, neither present charge nor conformational changes to the polypeptide, constitute further embodiments of the present invention. For example, it is believed that the exchange of an isoleucine for a leucine residue would have little or no effect on the functionality of the polypeptide Iα. It is also contemplated that fragments of Iα may be functional as well, and thus such fragments define further embodiments of the present invention.

Suitable sequences of DNA and/or RNA for constructing a cloning approach to synthesis of Iα may be identified by reverse translation and transcription of the amino acid sequence of Iα [SEQ ID NO:1], using the genetic code. Either or both of the DNA strands, i.e., the "sense" and "anti-sense" strands, may be usefully employed in the genetic engineering of clones for synthesis of Iα. Similarly, the RNA sequence may constitute the "sense" or "anti-sense" strands, as well. Accordingly, the present invention may be viewed as embodied in the RNA or DNA sequences recited and/or referred to herein.

Any suitable means may be applied for generating the RNA molecules having any of the following sequences:

```
CCN UCN GAR GGN AAR AUH AAR CAY UCN GGN CGN AUH UCN UUY  [SEQ ID NO:2]

UGY UCN CAR UUY UCN UGG AUH AUG CCN GGN ACN AUH AAR GAR

AAY GAR GAR UUY
``` wherein A is adenine, G is guanine, U is uracil, C is cytosine, W is A or U, Y is C or U, R is A or G, H is A, C or U, and N is G, A, C or U, and the symbols are organized in triplets to reflect the codons as translated in an organism. This RNA-related nomenclature is used hereinbelow for SEQ ID NO:5 and SEQ ID NO:6 as well.

Other RNA sequences that, upon translation, provide the same polypeptide sequence or its functional equivalent are contemplated hereby as well. For example, the triplet UCN can be replaced by the triplet AGY and the triplet CGN can be replaced by the triplet AGR, and yet result in no change in the resultant polypeptide sequence. In addition to the neutral sequence differences identified at the RNA level, as provided herein, nucleotide changes that provide conservative changes to the resultant amino acid sequence, as discussed above, are contemplated as well. Thus, for example, the triplet AUH, which encodes the amino acid isoleucine, may be replaced by the triplet CUN, which encodes the isomeric amino acid leucine, without significant effect on the functioning of the claimed polypeptide. Any of such sequences may be ligated into a suitable nucleic acid vector for propagation and expression in a suitable cellular or viral host, using methods well-known in the art.

The genetic complement of the aforestated RNA molecules, i.e., the anti-sense RNA, and the DNA counterparts to the sense and anti-sense RNA molecules are contemplated as embodiments of the present invention. Suitable means for generating the aforementioned sequences, their complements, or their DNA counterparts, as well as those disclosed hereinbelow, include in vitro polynucleotide synthesis of a manual or automated nature. Once constructed, such a sequence may be ligated to other nucleic acid sequences that specify signals for transcription or translation, and to yet other nucleic acid sequences useful as a vector for propagation and/or expression in bacterial, viral, or animal cells. Methods for preparing such nucleic acid constructs are well-known in the art. See Sambrook et al., supra.

The polypeptide or a suitable fragment thereof may be used per se or it may be associated with another compound, such as one or more amino acids, which may be covalently linked together as a second polypeptide, a proteoglycan, a proteolipid, a carbohydrate, or some other suitable macromolecule. Such associations of the inventive polypeptide with another macromolecule may be stabilized by means of covalent bonding, hydrogen bonding, adsorption, absorption, metallic bonding, van der Waals forces, ionic bonding, or other suitable inter- or intramolecular bonds or forces, or any combination thereof. For example, polypeptide Iα may effectively be enlarged by the covalent addition of one or more amino acids to the carboxy or amino terminus, or both termini, so long as its essential characteristic of binding to activating molecules for chloride ion efflux in CFTR-mutated cells is retained. A preferred form of the inventive polypeptide comprises the covalent linkage of the polypeptide to a suitable affinity chromatography matrix, such as cellulose, including m-aminobenzyloxymethylcellulose, bromoacetylcellulose, carboxymethylcellulose hydrazide, and cellulose cyclic-carbonate; 6-aminohexanoic acid; sepharose, including sepharose 4B, sepharose 6 MB, sepharose 6B, and thiol-sepharose 4B; beads composed of hydrophilic acrylic, polyacrylamide, and agarose; and linear polyacrylamide.

Suitable reactive moieties, such as hydrazides, carbonates, and the like, and suitable activators, such as cyanogen bromide, carbonyldiimidazole, chloroformates, and the like, may be applied to the aforementioned affinity chromatography matrices, using methods and materials well-known to the art, as provided, for example, by the 1993 Sigma Chemical Company catalog at pages 1612–1618 and other sources.

Figure 3A:
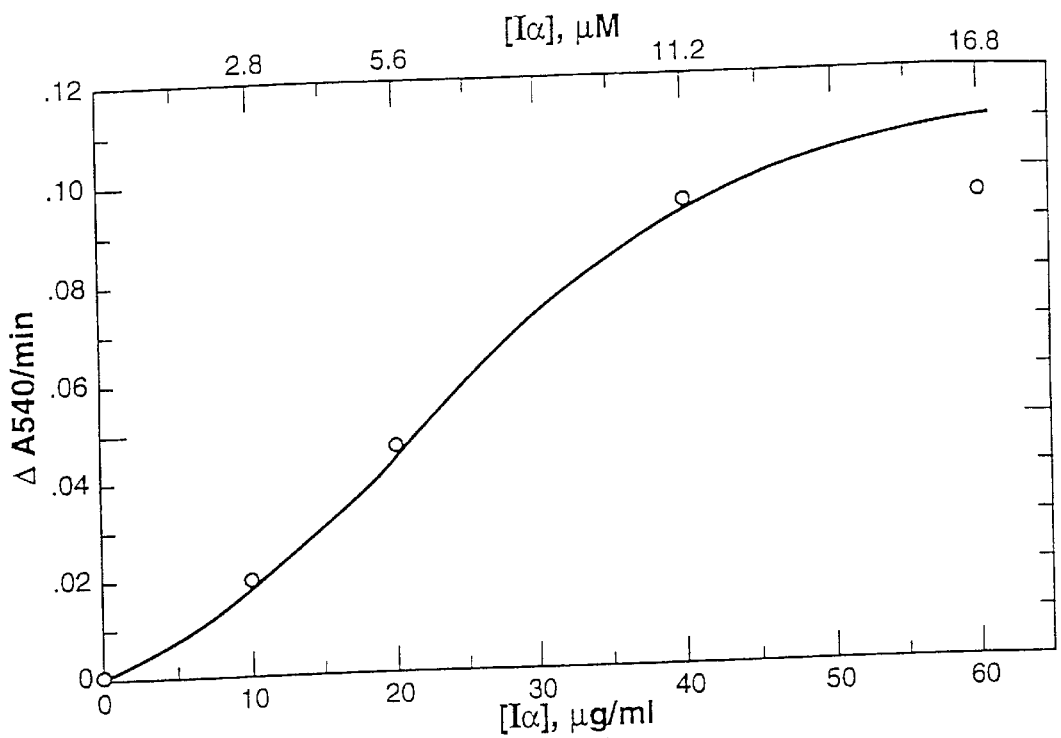
FIG. 3A is a graph that depicts the aggregation of chromaffin granules in the presence of varying concentrations of the Iα polypeptide. The units of the x-axis represent the concentration of Iα polypeptide (μg/ml) and the units of the y-axis represent change in turbidity (A540 nm). Reactions were performed as for generating the data of FIG. 2; the initial rate was calculated for each concentration of Iα.
Figure 3B:
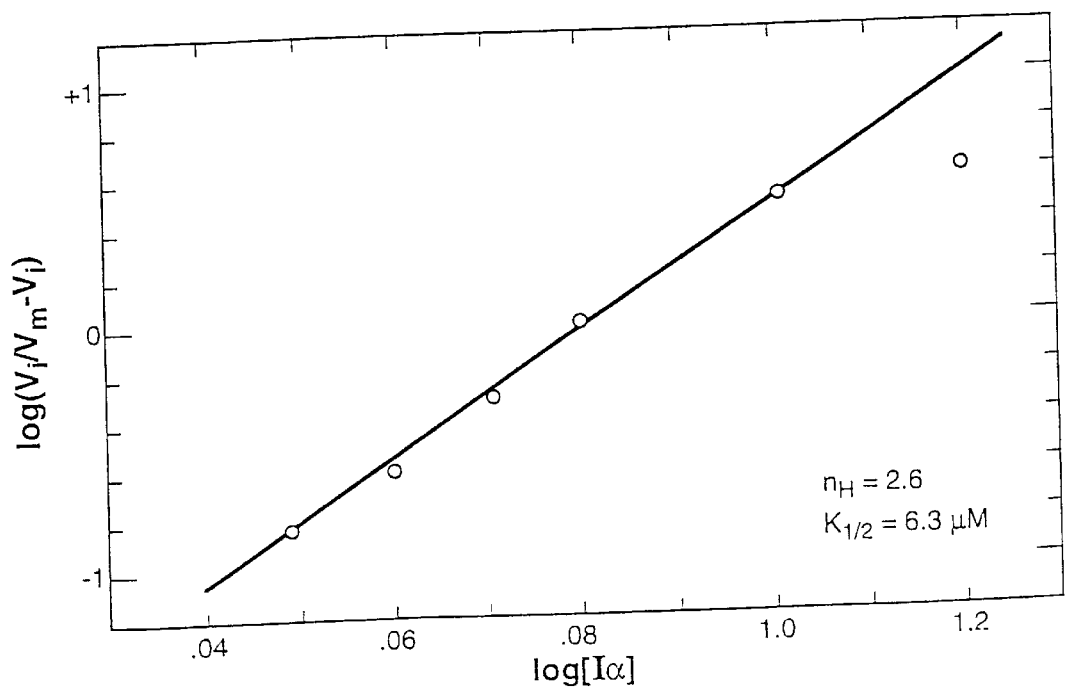
FIG. 3B is a Hill plot for the data displayed in FIG. 3A. The $V_{max\ app}$ was estimated from the linear extrapolation of the Lineweaver-Burk plot (log $(V_i/V_m-V_i)$ versus log [Iα]) of the data, and the ratio of velocities was computed for each condition. The slope (2.6) is the Hill coefficient ($n_H$).
Figure 4A:
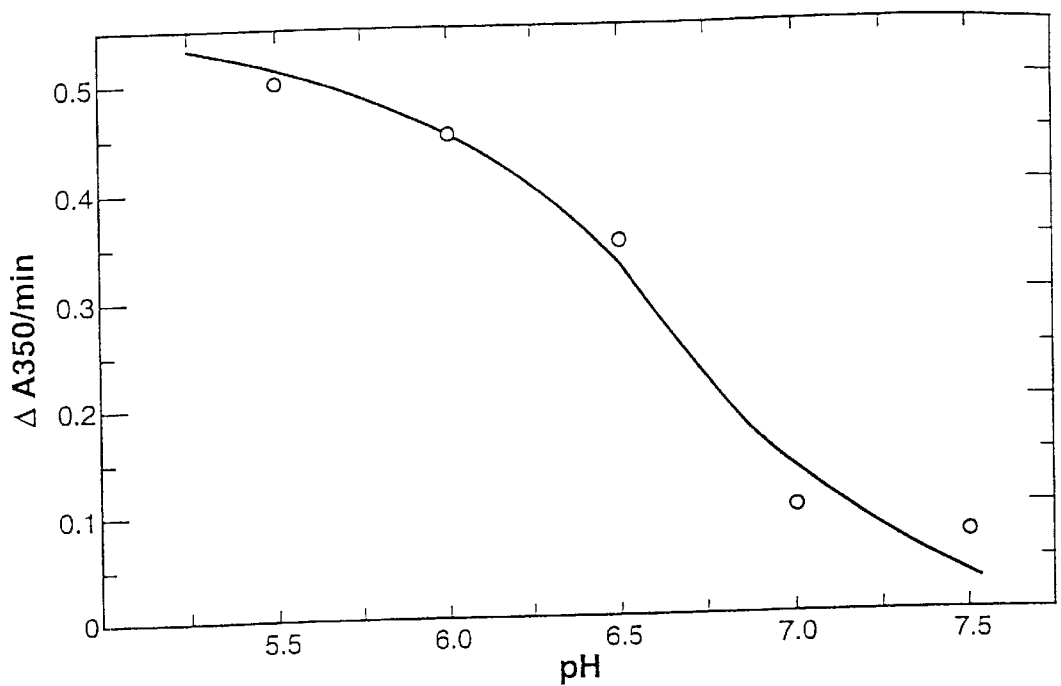
FIG. 4A is a graph that depicts phosphatidylserine liposome aggregation (y-axis is $\Delta A_{350}$/min) by Iα at different pH values (x-axis). The concentration of Iα is 2 μg/ml (0.6 μM).

Properties of the Iα polypeptide include (1) commencing or causing the aggregation of bovine chromaffin granules in the presence of about 1 mM $CaCl_2$; having an apparent $k_{1/2}$ of 22.2 μg/ml or 6.3 μM (see FIGS. 3A and 3B); (2) having activity in a pH range of from about 5.5 to about 7.5, wherein 50% activity was measured at about 6.75 (see FIG. 4A); (3) having a synergistic effect on commencing or causing the aggregation of liposomes when combined with a compound that activates chloride ion efflux in cells having the ΔF508 mutation, which compounds include CPX, caffeine, and N,N-diallylcyclohexylxanthine (DAX) (see FIGS. 5, 6, and 7, respectively); (4) having no increased effect on commencing or causing the aggregation of liposomes when combined with a compound that is known not to activate chloride ion efflux in cells having the ΔF508 mutation, which compounds include 2-thio-CPX and isobutylmethylxanthine (IBMX), among others; (5) having a biphasic interaction with adenosine wherein at lower adenosine concentrations of 70 and 100 nM there was a modest increase in the aforementioned liposome aggregation reaction driven by polypeptide Iα, at higher adenosine concentrations such increase in activity was not seen, and at 1 μM and greater the aggregation activity was suppressed; and (6) having an apparent $K_D$ of 69±27 nM with respect to CPX, a xanthine derivative known to activate chloride ion efflux from ΔF508 cells.

The present invention also provides certain other CFTR polypeptides that are contiguous to polypeptide Iα but, nevertheless, have characteristics that are significantly different. Polypeptide Iβ is a sequence of amino acids included in the CFTR protein from position 509 to position 539, and has the following sequence:

NH₂-GVSYDEYRYRSVIKACQLEEDISKFAEKDNI-COOH  [SEQ ID NO:3]

Polypeptide Io is another sequence of amino acids included in the CFTR protein at from position 500 to position 531, and has the following sequence:

NH₂-GTIKENEEFGVSYDEYRYRSVIKACQLEEDIS-COOH  [SEQ ID NO:4]

These polypeptides are contiguous or partially overlap polypeptide Iα, yet neither of these polypeptides drives the aggregation of chromaffin granules or synthetic liposomes, nor has any effect on the activity of polypeptide Iα as disclosed herein or chloride ion efflux-activating xanthine derivatives. Analogously to the discussion above relating to conservative amino acid changes of Iα, it is contemplated that polypeptides having such conservative changes are further embodiments of the present invention.

The Iβ and Io polypeptides may be prepared and used as free polypeptides, as fragments thereof, or associated with another macromolecule, as discussed hereinabove for the Iα polypeptide. The Iβ and Io polypeptides may be used in affinity chromatography, and used as a negative control relative to the Iα polypeptide.

As with the Iα polypeptide discussed above, suitable sequences of RNA and/or DNA corresponding to Iβ and Io may be identified by reverse translation/transcription of the amino acid sequences of the respective polypeptide, using the genetic code. Accordingly, any suitable means may be applied for generating the RNA molecules having any of the following sequences:

sequence, the RNA complement of SEQ ID NO:5 and SEQ ID NO:6, as well as the DNA counterpart sequences predicated thereon, are included as embodiments of the present invention, and may be determined by the application of the conventional genetic code by an ordinary artisan.

The aforementioned Iα, Iβ and Io polypeptides or their functional equivalents may be used in a method for identifying a CFTR-binding compound. Such a method comprises contacting a putative CFTR-binding compound to polypeptide Iα [SEQ ID NO:1] under conditions sufficient to allow for binding of the putative CFTR-binding compound to said polypeptide Iα, and determining, by any suitable means, whether such binding occurred, which would be indicative that the putative CFTR-binding compound was indeed a CFTR-binding compound. By CFTR-binding compound, it is intended that the compounds to be identified by the present method will interact with a cell's CFTR, preferably a mutated CFTR such as ΔF508, such that the chloride ion efflux mediated by the CFTR will be increased, and perhaps restored. Such interaction between a CFTR-binding compound and the CFTR protein may be provided by any suitable combination of ionic, hydrophobic, and van der Waals bonds or forces, as a function of the sequence of the amino acids of the CFTR and the physico-chemical characteristics of the CFTR-binding compound. For the identification of such CFTR-binding compounds, preferably those that are candidates for testing as CF-directed therapeutic agents, it is useful to test for positive effect of affinity to polypeptide Iα and, preferably, also for neutral or negative effect of no affinity to polypeptide Iβ and/or Io. The conditions used for such affinity assays for identifying CFTR-binding compounds can be optimized using conventional techniques well known in the art. The method may identify any suitable compound that selectively binds to Iα, for example, but not to Iβ, for example, wherein the compound is a hydrocarbon, including, but not limited to, a protein, a lipid, a nucleic acid, or any combination thereof.

Among the effects of a CFTR-binding compound of interest are the following: (1) commences or causes the aggregation of synthetic polysaccharide liposomes when

Iβ:

GGN GUN UCN UAY GAY GAR UAY CGN UAY CGN UCN GUN AUH AAR  [SEQ ID NO:5]

GCN UGY CAR UUR GAR GAR GAY AUH UCN AAR UUY GCN GAR AAR

GAY AAY AUH

Io:

GGN ACN AUH AAR GAR AAY GAR GAR UUY GGN GUN UCN UAY GAY  [SEQ ID NO:6]

GAR UAY CGN UAY CGN UCN GUN AUH AAR GCN UGY CAR UUR GAR

GAR GAY AUH UCN

Analogously to the Iα sequence, other sequences that encode the same or functionally equivalent sequences as compared to SEQ ID NO:5 and SEQ ID NO:6 are contemplated as well. For example, the triplets UCN, GCN, and UUR may be replaced by AGY, AGR, and CUN, respectively, without any resultant amino acid sequence differences. In addition, nucleotide sequences that result in neutral amino acid charges, as discussed above with respect to the Iα sequences, are contemplated as additional embodiments of the present invention. Moreover, as with the Iα added to a preparation of (i.e., composition comprising) such liposomes (described in Example 1); (2) commences or causes the aggregation of chromaffin granules when added to a preparation of (i.e., composition comprising) such chromaffin granules (described in Example 1); and (3) commences or causes the aggregation of the aforementioned liposomes at an increased rate when an activator of chloride ion efflux of a ΔF508 cell is added to such liposomes (see FIGS. 5–7). Activators of chloride ion efflux useful in the context of the present invention include CPX, caffeine, N,N-diallylcyclohexylxanthine, and other suitable compounds. No chloride ion efflux activator that has been tested in conjunction with Iα has failed to exhibit the phenomenon of increased rate of liposome aggregation relative to the effect of Iα alone.

The present invention further provides a method of treating cells having a reduced apical Cl⁻ conductance, such as cystic fibrosis cells, and provides novel compounds and pharmaceutical compositions thereof useful in the context of the present inventive method. Specifically, the treatment method involves contacting cells having a reduced apical Cl⁻ conductance with a therapeutically effective quantity of a compound that has little or no affinity for adenosine cell receptors, particularly either the $A_1$-adenosine cell receptor or the $A_2$-adenosine cell receptor, yet stimulates Cl⁻ efflux. In particular, the method involves contacting such cells with a compound having the formula

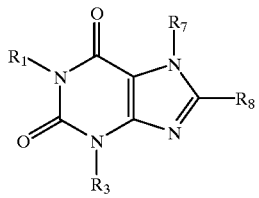

wherein $R_1$ and $R_3$ are the same and are $C_1$–$C_6$ alkyl or $C_1$–$C_6$ alkenyl, $R_7$ is $C_1$–$C_6$ alkyl or hydrogen, and $R_8$ is $C_4$–$C_8$ cycloalkyl, or a therapeutically effective derivative thereof. Such compounds may be characterized with respect to their respective affinity for an adenosine receptor, such as the $A_1$- or $A_2$-adenosine receptor. In particular, the affinities of such compounds can be expressed with respect to a $K_i$ value, such as having a $K_i$ of greater than or equal to 0.01. Preferred compounds have a $K_i$ of at least 0.05. Such preferred compounds include those where $R_1$ and $R_3$ are methyl, propyl or allyl, $R_7$ is methyl or hydrogen, and $R_8$ is cyclopentyl or cyclohexyl, and in particular are one of the group consisting of 1,3-dipropyl-7-methyl-8-cyclohexylxanthine, 1,3-dipropyl-7-methyl-8-cyclopentylxanthine, 1,3-diallyl-8-cyclohexylxanthine, and 8-cyclohexyl caffeine.

The present inventive method has particular utility in the treatment of cystic fibrosis cells. The method is especially preferred in the treatment of cystic fibrosis cells that have a deletion involving phenylalanine at amino acid position 508 of the cystic fibrosis transmembrane regulator, in particular those cystic fibrosis cells found within a mammal, such as a human patient.

The compound used in the present inventive method is preferably one that does not have phosphodiesterase activity. It is also preferred that the therapeutically effective quantity of the compound is nontoxic. Most preferably, the compound, itself, is nontoxic or, if toxic, provides a benefit that outweighs such toxicity. It is further preferred that the compound of the present invention has a low level of affinity for any adenosine receptor (such as having a $K_i$ of greater than or equal to about 0.01 mM) as recited above and exemplified below with respect to $A_1$- or $A_2$-adenosine receptors. With respect to $A_3$-adenosine receptors, it is not likely the compounds of the present invention have substantial affinity thereto because most xanthines cannot be accommodated in the $A_3$-adenosine receptor binding site. van Galen et al., *Medicinal Res. Rev.*, 12, 423–471 (1992). Especially preferred compounds for use in the present inventive method are 1,3-dipropyl-7-methylcyclopentylxanthine (DP-CPX), 1,3-diallyl-8-cyclohexylxanthine (DCHX), and cyclohexyl caffeine (CHC); the most preferred compound is DCHX.

Such compounds and pharmaceutical compositions containing same, heretofore undisclosed, are themselves embodiments of the present invention. In particular, compounds of the present invention first disclosed herein have the formula

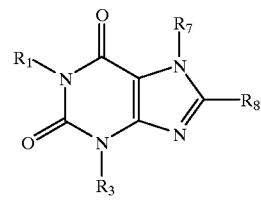

wherein (a) $R_1$ and $R_3$ are the same and are methyl or allyl, $R_7$ is ethyl, cyclopropylmethyl or hydrogen, and $R_8$ is cyclohexyl, provided that $R_1$ is allyl when $R_7$ is hydrogen and $R_1$ is methyl when R7 is ethyl or cyclopropylmethyl, or (b) $R_1$ and $R_3$ are both methyl, and $R_7$ is hydrogen or methyl, and $R_8$ is cyclohexylmethyl or cycloheptyl. A preferred compound according to the aforementioned structure is compound 17, i.e., 1,3-diallyl-8-cyclohexylxanthine (DCHX).

Alternatively, or additionally, a pharmaceutically acceptable derivative of DP-CPX, CHC, or DCHX, for example, or combinations thereof as yet further examples, may be used in the present inventive method, which provide yet another embodiment of the present invention. It is desirable that such a derivative have equivalent therapeutic effectiveness in the context of the present inventive method of treatment.

The compound useful in the present inventive method may be administered by any suitable means. One skilled in the art will appreciate that many suitable methods of administering the compound to an animal in the context of the present invention, in particular a human, are available, and, although more than one route may be used to administer a particular compound, a particular route of administration may provide a more immediate and more effective reaction than another route.

The compound is preferably administered directly to the lung of a patient. Preferably, the compound is administered as a pharmaceutically acceptable aqueous solution. It is even more preferable that the compound be administered as an aqueous pharmaceutical solution containing from about 0.001 to about 0.01% w/w of the compound. A pharmaceutically acceptable aerosol is another preferred means of administration. The aerosol preferably contains from about 0.001 to about 0.01% w/w of the compound.

The compound also may be administered orally. In such a case, the compound will be generally administered in an amount of from about 0.1 to 1 mg/kg body weight per day. A preferred amount of the inventive compound for oral administration is about 0.1 mg/kg body weight per day. Other routes of administration, such as intravenous and intraperitoneal administration, are also possible.

The compound should be administered such that a therapeutically effective concentration of the compound is in contact with the affected cells of the body. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The size of the dose also will be determined by the existence, nature, and extent of any adverse side effects that might accompany the administration of a particular compound and the particular route of administration employed with a particular patient. In general, the compounds of the present invention are therapeutically effective at low doses. The effective dosage range is from about 30 nM to about 100 nM in the blood. Accordingly, the compounds will be generally administered in relatively low doses.

The compound may be administered in a pharmaceutically acceptable carrier. The present invention encompasses pharmaceutical compositions comprising the present inventive compounds and pharmaceutically acceptable carriers. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for administration by inhalation include aerosol formulations placed into pressurized acceptable propellants, such as dichlorodifluoromethane, propane, nitrogen, and the like. The active agent may be aerosolized with suitable excipients.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared for sterile powders, granules, and tablets of the kind previously described.

The desirable extent of the induction of Cl⁻ efflux from cells will depend on the particular condition or disease being treated, as well as the stability of the patient and possible side effects. In proper doses and with suitable administration of certain compounds, the present invention provides for a wide range of activation of the rate of chloride ion efflux, e.g., from little activation to essentially full activation.

The present invention is expected to be effective in the treatment of all conditions, including diseases, that may be characterized by a reduced cellular apical Cl⁻ conductance. In particular, the present invention is expected to have utility in the treatment of chronic obstructive pulmonary diseases, especially cystic fibrosis.

The following examples serve to further illustrate the present invention and are not intended to limit the scope of the invention.

EXAMPLE 1

This example illustrates the methods used to assess the membrane-directed activity of certain CFTR polypeptides, and the results thereof.

Liposome aggregation assay: Phosphatidylserine ("PS", obtained from Avanti) was dissolved in chloroform, and small unilamellar liposomes were prepared by the extrusion process known in the art. A Lipex machine was used to extrude the PS in a buffer consisting of 10 mM Na-HEPES, pH 7.2 and 1 mM EDTA. The liposomes were diluted to a final optical density at 540 nm of 0.01 and incubated with different concentrations of the different polypeptides and/or chloride ion efflux-activating compounds.

Chromaffin granule aggregation assay: Adrenal glands were obtained from a local abattoir and transported to the laboratory on ice within 2 hours of slaughter. Tissue was processed as described in Brocklehurst et al. in *Polypeptide Hormones: A Practical Approach* (Oxford Univ. Press, K. Siddle and J. Hutton, eds., 1990) at pp. 237–255. Chromaffin granules were purified on a step gradient of metrizamide using standard procedures. After resuspension, the granule aggregation assay was performed as described (Brocklehurst et al., supra), and the synexin activity was assessed from the initial rate of optical density increase at 540 nm. Briefly, the assay was carried out at room temperature in a 1 ml quartz cuvette containing the chromaffin granule suspension in 0.3 mol/l sucrose, 40 mmol/l histidine buffer, pH 6.0, synexin and variable amounts of calcium chloride.

Preparation of CFTR Polypeptides: Polypeptides were synthesized at the Yale University Department of Molecular Biology and Biophysics by standard solid phase methods. The polypeptides were purified by reverse phase HPLC, and the sequences were verified by direct chemical sequencing, amino acid analysis, and by mass spectroscopy, using standard methods well-known in the art. The specific polypeptides were Iα [SEQ ID NO:1], Iβ [SEQ ID NO:3], and Io [SEQ ID NO:4].

Figure 2:
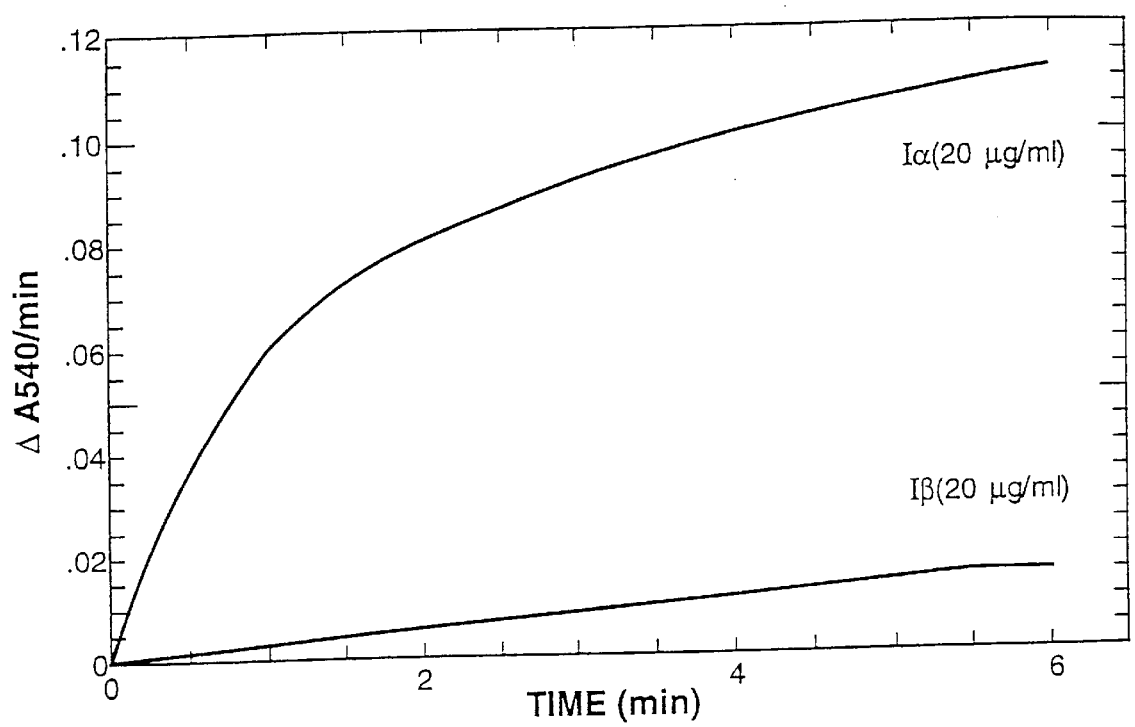
FIG. 2 is a graph that depicts the aggregation of chromaffin granules by certain CFTR polypeptides at a concentration of 20 μg/ml (5.2 μM), at pH 6.0 and 1 mM $Ca^{++}$. The units of the x-axis represent minutes of time and the units of the y-axis represent change in turbidity (Δ540 nm).

Aggregation of chromaffin granules and liposomes by Iα [SEQ ID NO:1]: As shown in FIG. 2, polypeptide Iα was found to drive aggregation of bovine chromaffin granules in the presence of 1 mM $CaCl_2$. By contrast, the contiguous polypeptide Iβ [SEQ ID NO:3] was found to be essentially inactive in the chromaffin granule aggregation assay. Similarly, the overlapping polypeptide, Io [SEQ ID NO:4], was also found to be inactive. These data thus appear to indicate that the action of Iα is specific to the Iα sequence.

A titration of the Iα activity, illustrated in FIG. 3A, shows that the $k_{1/2}$,appwas 22.2 µg/ml or 6.3 µM. A Hill plot of these data (see FIG. 3B) indicated that the Hill coefficient ($n_H$) was 2.6. Similar data were observed using phosphatidylserine liposomes as an aggregation target, and a detailed titration over the pH range between pH 5.5 and 7.5 indicated that the pH for 50% activity was ca. 6.75 (see FIG. 4A).

Figure 4B:
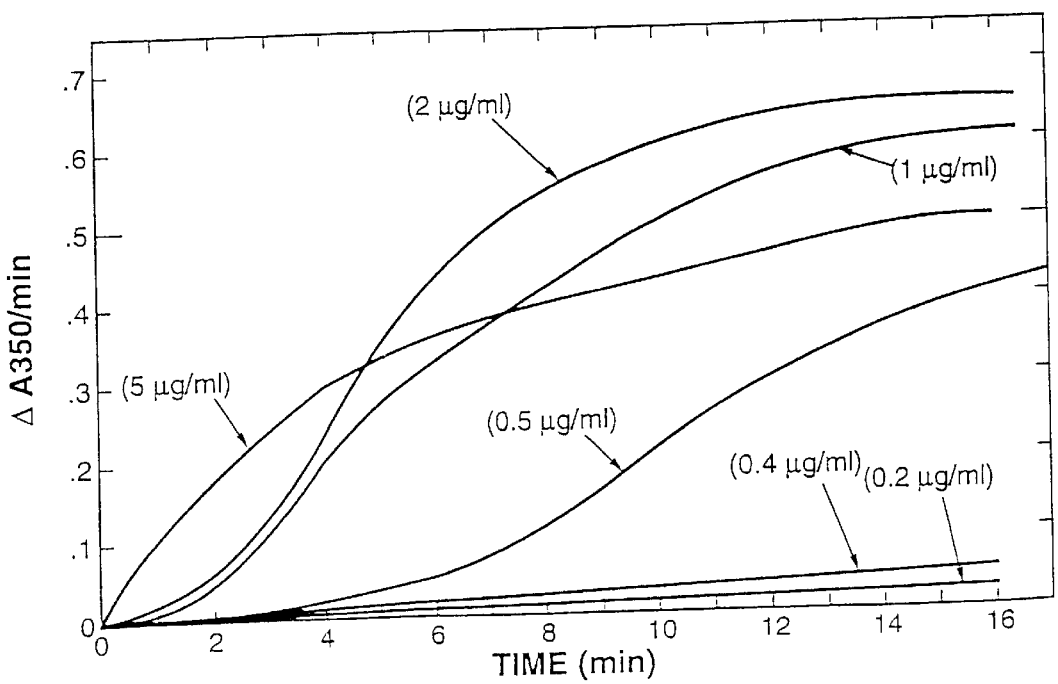
FIG. 4B is a graph that depicts phosphatidylserine liposome aggregation (y-axis is $\Delta A_{350}$/min) by lower concentrations of Iα polypeptide measured over time (x-axis in minutes).

Aggregation of PS liposomes by low concentrations of Iα: As shown in FIG. 2, the aggregation reactions at high polypeptide concentrations were initiated promptly, and followed an apparent first order process that effectively plateaued within 5–10 minutes. The cooperative character of the aggregation reaction driven by Iα is quantitatively manifest by the Hill coefficient (see FIG. 3A), which graphically shows that at lower polypeptide concentrations the initial rates of aggregation became small rather abruptly. However, at much longer time periods it became evident that a significant aggregation reaction still occurred, albeit with complex kinetics. As shown in FIG. 4B, the kinetics involved an initial lag phase of some 8–10 minutes, followed by a rising phase and a plateau. The conversion from an apparent first order process to the more complex process occurred below 2 μM of Iα polypeptide, and the complex processes were clearly evident in a dose dependent manner between 0.4 and 2 μM. Below about 0.4 μM, all activity virtually ceased.

Accordingly, Iα drives the above-described membrane aggregation phenomena whereas the adjacent (Iβ) or partially overlapping (Io) polypeptide sequence, with respect to CFTR, does not drive such aggregation. The effective internal negative control clearly illustrates the existence of a special functional property located on the CFTR at the Iα site, which property clearly implicates membrane involvement.

EXAMPLE 2

This example illustrates the specific binding of certain chloride ion efflux activating compounds to Iα, and the inability of certain compounds that do not activate chloride ion efflux to bind to Iα.

CPX was used as a representative compound known to activate chloride ion efflux from ΔF508 mutant cells. Stock solutions of CPX were prepared in DMSO in the millimolar concentration range. The Iα polypeptide (100 nM final polypeptide concentration) was dissolved in 100 μl of a buffer solution containing 50 mM TRIS (pH=7.0), 300 mM sucrose, and 10 mM glutathione. After 1 hour of incubation at 37° C., 1–100 nM $^3$H-CPX (ICN, specific activity=109 C$_i$/mole) was added and incubated for a further 15 minutes. For displacement studies, unlabeled CPX, or other xanthine antagonists and nucleotides, were added to the incubation mixture before the radioactive probe. The mixture was then filtered through a nitrocellulose (NC) membrane (Schleicher & Schuell) by using a standard dot blot apparatus. Non-specific binding of $^3$[H]-CPX to NC filters was reduced by blocking filters with 0.3% polyethyleneimine (PEI). The dot blots were then washed five times with 200 μl TRIS buffer-NaCl solutions (50 mM TRIS pH=7.0, 150 mM NaCl), radioactive spots were cut out, and the total radioactivity was determined by liquid scintillation counting. Specific $^3$H-CPX binding to Iα was determined by subtracting the non-specific binding, defined by preincubation with 10 μM unlabelled CPX, from total binding.

The binding of $^3$H-CPX to Iα was a saturable function of the CPX concentration. A fit of the data to a Scatchard plot showed the $K_{D,app}$ to be 69±27 nM (n=4). The $B_{max}$, estimated from the Scatchard plot intercept, indicated that the mole fraction of bound Iα polypeptide was less than $\frac{1}{2000}$. Displacement of binding was effected by CPX, caffeine, and DAX, all known chloride ion efflux activators, but was not effected by IBMX or 2-thio-CPX, which are known not to activate chloride ion efflux.

These data indicate that a chloride ion efflux activator can bind specifically to Iα, thereby suggesting that the mechanism of CPX activation of cells bearing the CFTR (ΔF508) mutation may be by interaction with the CFTR molecule itself. Moreover, because of the specificity of chloride ion efflux activators to bind and non-chloride ion efflux activators not to bind to Iα, these data illustrate the utility of this method to identify further CFTR-binding proteins that may have a therapeutic effect on CF cells.

EXAMPLE 3

This example illustrates the effect of CPX on PS liposome aggregation driven by Iα.

The impact of CPX on PS liposome aggregation that was driven by Iα was investigated. The study was done using concentrations of CPX of between 1 and 30 nM (activation noted in ΔF508 containing cells), between 30 and 100 nM (maximum activation noted in the aforementioned cells), on up to 1000 nM (inhibition of activation noted in the aforementioned cells).

Figure 5:
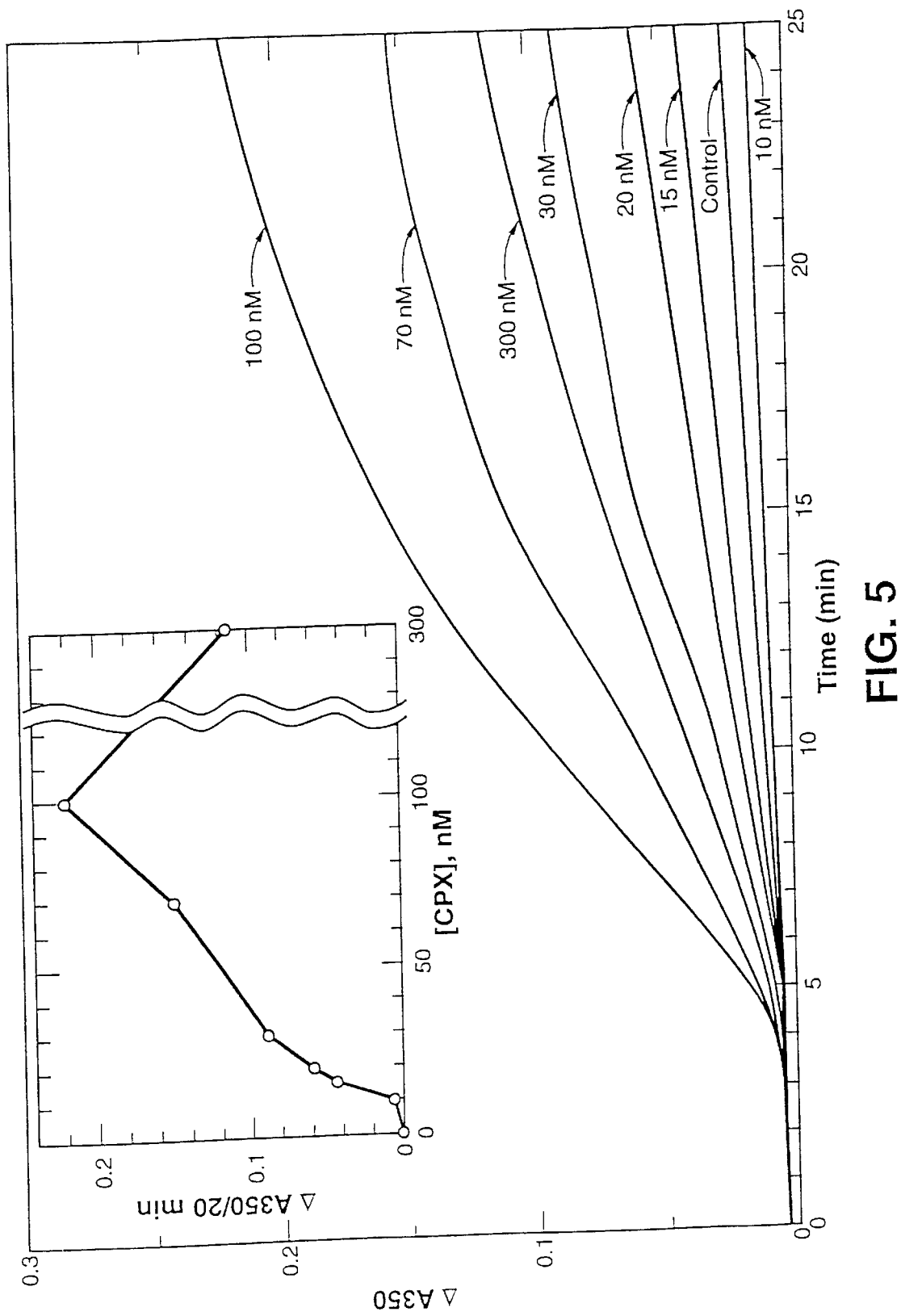
FIG. 5 is a graph that depicts the effect of CPX (x-axis in min) on aggregation of phosphatidylserine liposomes driven by Iα polypeptide (y-axis is $\Delta A_{350}$/min). The inset graph depicts the concentration dependence for CPX activation at the 20 minute time point, wherein the y-axis is $\Delta A_{350}$/20 min and the x-axis is concentration of CPX in nM.

As shown in FIG. 5, liposome aggregation driven by 0.5 μg/ml (0.18 μM) Iα alone was very modest. However, with increases in CPX concentration, the aggregation reaction was progressively activated after a lag of approximately 5 minutes. The maximum rate and extent of aggregation was observed at 100 nM CPX, and it thereafter fell when the CPX concentration was raised to 300 μM. The inset to FIG. 5 shows the extent of the reaction at a 20 minute time point.

Accordingly, these data show a parallel between the concentration-dependent behavior of CPX with (1) ΔF508 containing cells and (2) Iα aggregation.

EXAMPLE 4

This example illustrates the effect of other xanthines on PS liposome aggregation driven by Iα. Included in the study were certain xanthine derivatives known to activate chloride ion efflux in ΔF508 (e.g., caffeine and N,N-diallylcyclohexylxanthine (DAX)) or not to activate such chloride ion efflux (e.g., 2-thio-CPX and isobutylmethylxanthine (IBMX)).

Figure 6:
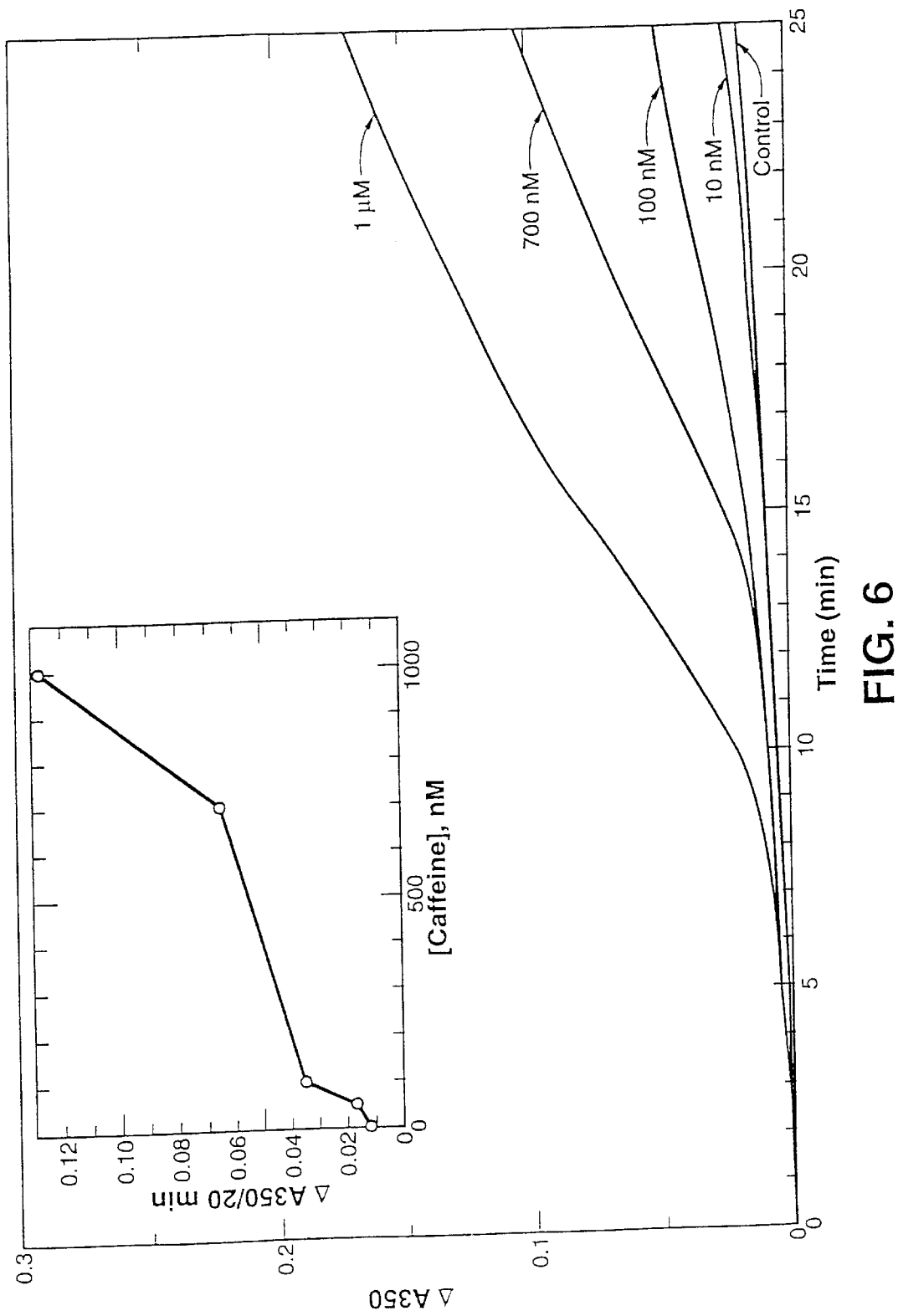
FIG. 6 is a graph that depicts the effect of caffeine (x-axis is min) on aggregation of phosphatidylserine liposomes driven by Iα polypeptide (measured on the y-axis as $\Delta A_{350}$/min). The inset graph depicts the concentration dependence for CPX activation at the 20 minute time point, wherein the y-axis is $\Delta A_{350}$/20 min and the x-axis is in nM concentration units of caffeine.

Results from a PS liposome aggregation assay are shown in FIG. 6. As is apparent from the graph, caffeine activates Iα aggregation with low potency, and does not appear to inactivate Iα aggregation at the highest concentrations. The inset to FIG. 6 shows the extent of the reaction at the 20 minute time point, such that the aggregation does not level off at all over the caffeine concentrations tested.

Figure 7:
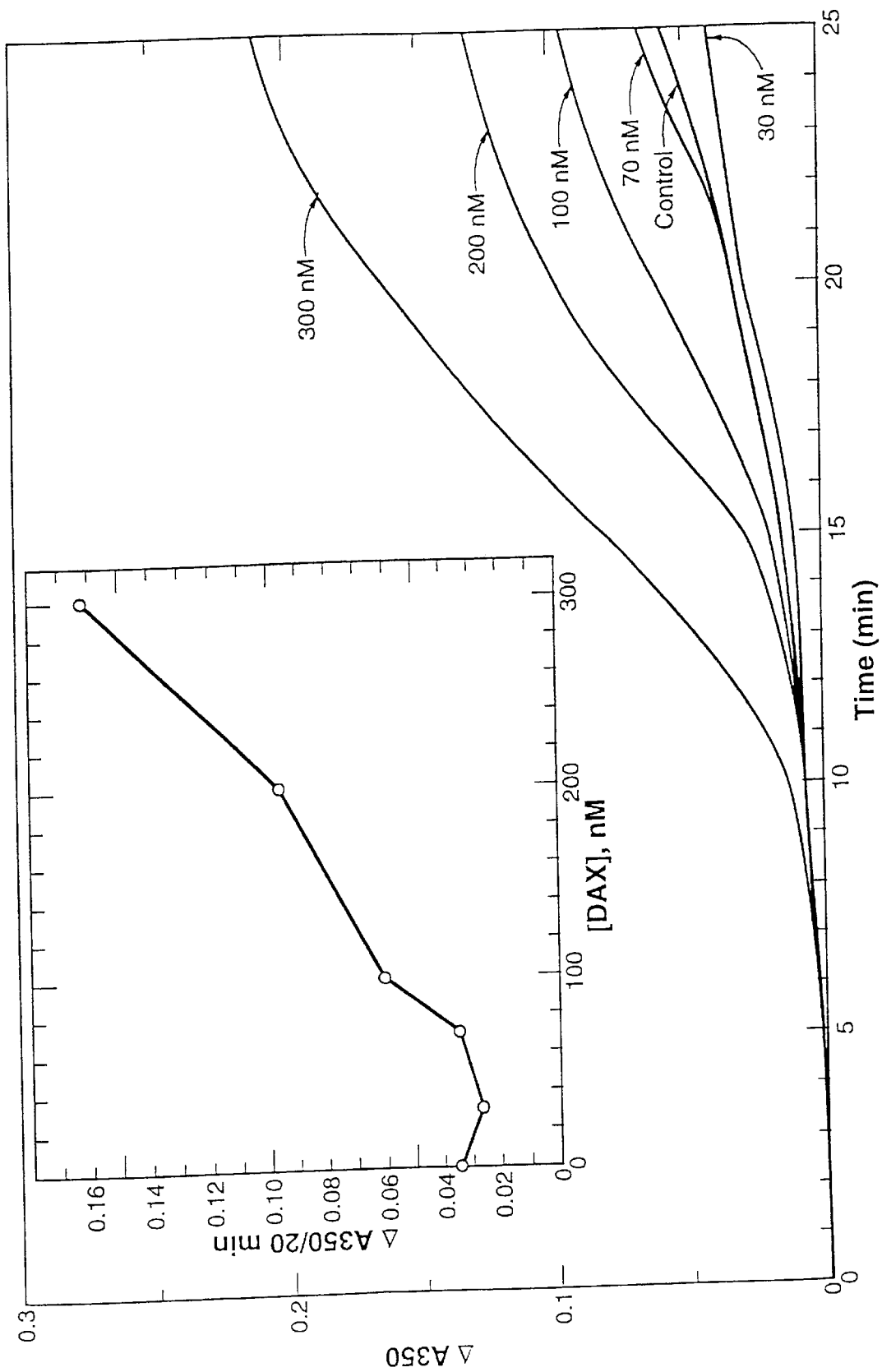
FIG. 7 is a graph depicting the effect of DAX concentration (x-axis is min) on aggregation of phosphatidylserine liposomes (y-axis, $\Delta A_{350}$/min) driven by Iα polypeptide. The inset graph depicts concentration dependence for DAX activation at the 20 minute time point, wherein the x-axis is nM units of concentration of DAX and the y-axis is in units of $\Delta A_{350}$/20 min.
Figure 8:
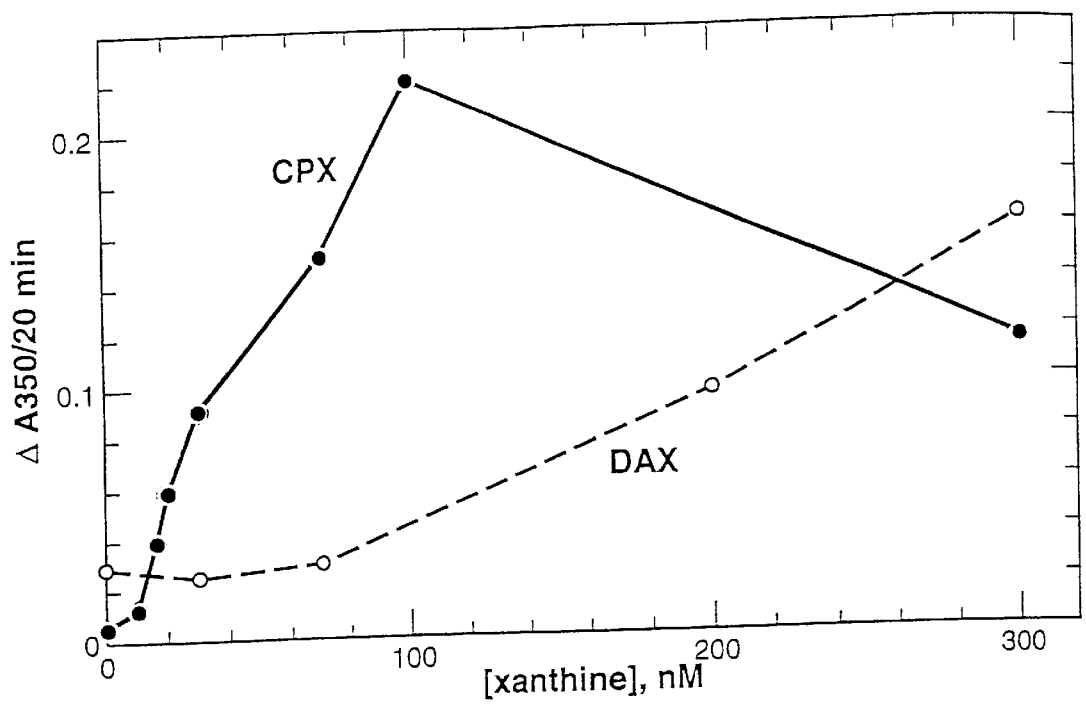
FIG. 8 is a graph that depicts the comparison of CPX and DAX activation of phosphatidylserine liposome aggregation by Iα polypeptide. The x-axis is in nM concentration units of CPX or DAX and the y-axis is in units of $\Delta A_{350}$/20 min.
Figure 9:
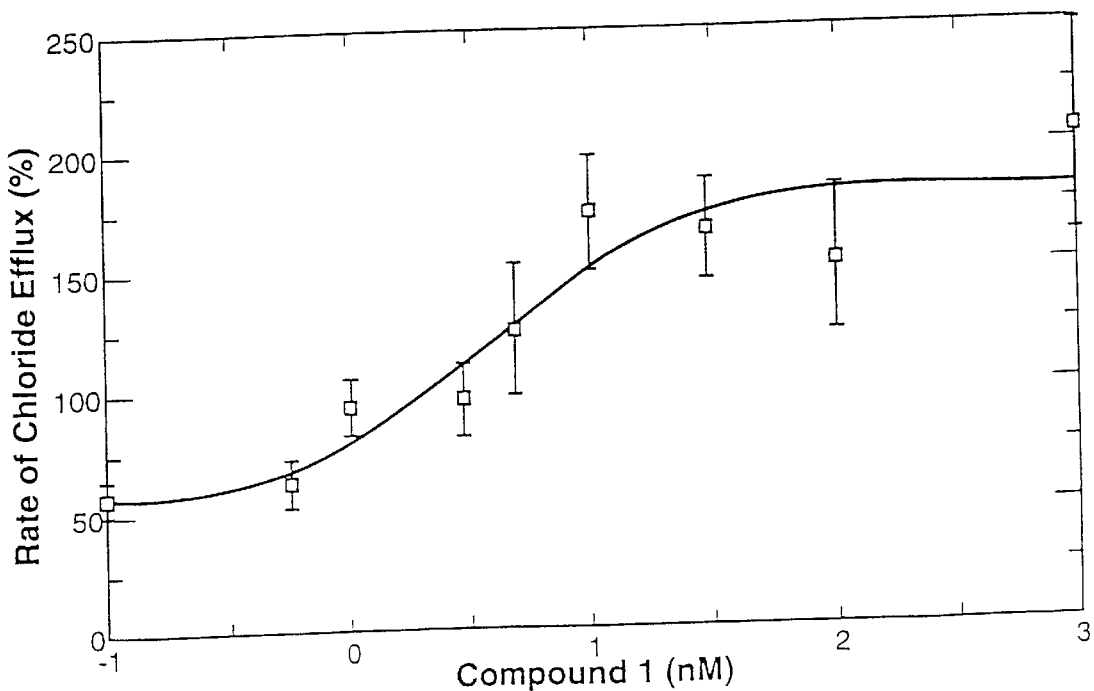
FIG. 9 depicts a graph of the results of $[^{36}Cl]^-$ efflux studies of CFPAC cells when placed in contact with compound 1 (theophylline). The x-axis represents the nanomolar concentration of compound 1, and the y-axis represents the rate of chloride efflux as a percentage of control.
Figure 10:
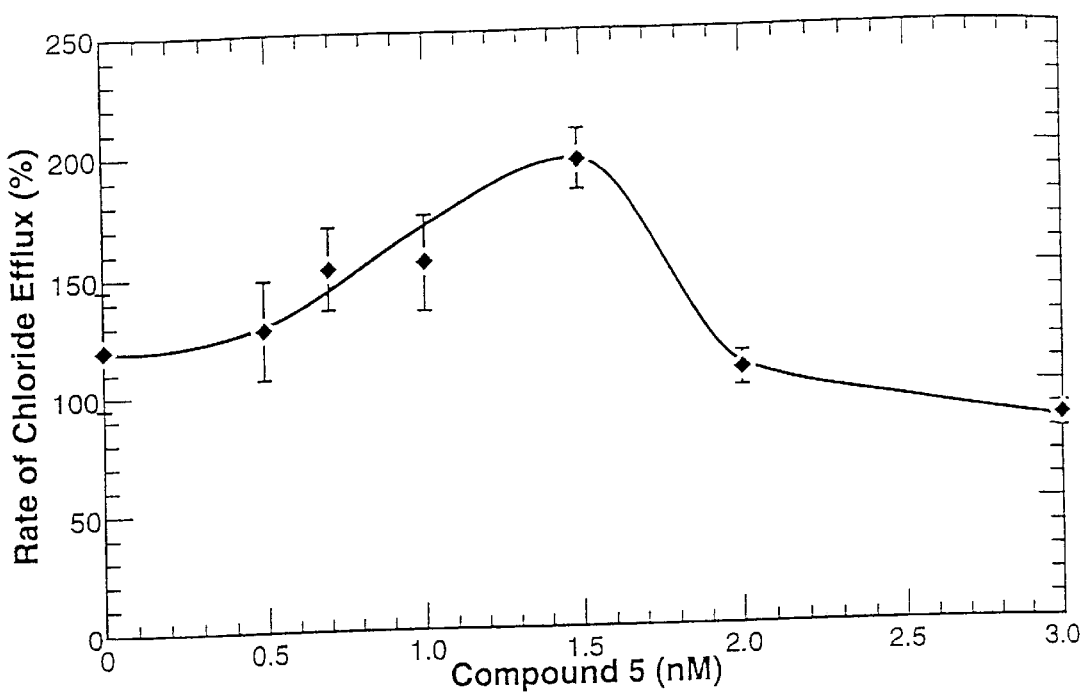
FIG. 10 depicts a graph of the results of $[^{36}Cl]^-$ efflux studies of CFPAC cells when placed in contact with compound 5 (CPX). The x-axis represents the nanomolar concentration of compound 5, and the y-axis represents the rate of chloride efflux as a percentage of control.
Figure 11:
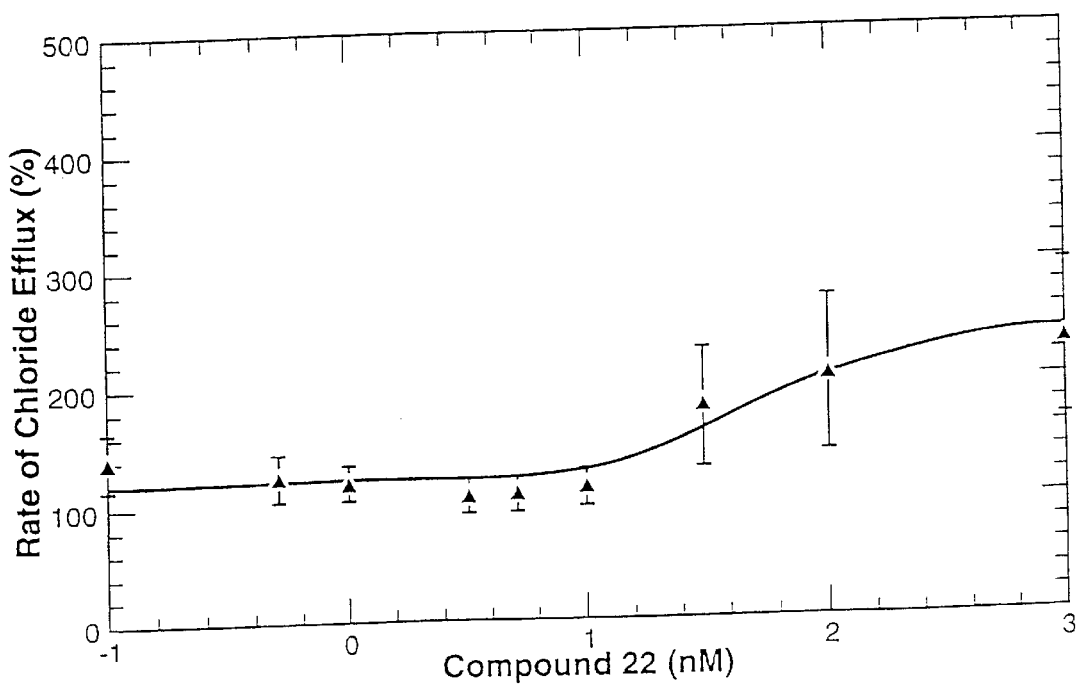
FIG. 11 depicts a graph of the results of $[^{36}Cl]^-$ efflux studies of CFPAC cells when placed in contact with compound 22 (8-cyclohexylmethyl caffeine). The x-axis represents the nanomolar concentration of compound 22, and the y-axis represents the rate of chloride efflux as a percentage of control.

In the case of DAX, the potency is in the range of CPX, but no inactivation is seen at concentrations as high as 300 nM (see FIG. 7). The inset to FIG. 7 shows the extent of the reaction at a 20 minute time point. From this perspective, one can compare both CPX and DAX on the same type of plot (FIG. 8), whereupon it can be seen that DAX is at least one-half a log less potent than CPX. However, the efficacies with respect to the chloride ion efflux of DAX and CPX are virtually the same. Higher concentrations of DAX were not possible because of solubility limits.

Inclusion of 2-thio-CPX and IBMX, compounds known to be inactive as activators of chloride ion efflux from cells bearing the ΔF508 mutation, in the liposome aggregation assay showed these compounds to be entirely inactive at potentiating liposome aggregation driven by Iα at concentrations up to 1 and 15 μM, respectively.

Accordingly, the Iα-driven PS liposome aggregation assay provides exactly parallel results with xanthine derivatives known to be active or inactive at chloride ion efflux activation.

EXAMPLE 5

This example illustrates the effect of adenosine on Iα-driven PS liposome aggregation.

Adenosine was included in a PS liposome aggregation assay. Adenosine had a modest but evident biphasic effect on the Iα-driven liposome aggregation reaction. At the lower concentrations of 70 and 100 nM, adenosine modestly activated the aggregation reaction. However, at higher concentrations, the activating effect was lost. At concentrations of 1 μM adenosine and greater the aggregation reaction was actually suppressed below the already low control levels. These data thus indicate that the xanthines, CPX and DAX apparently interact with a site on the Iα polypeptide with affinity for adenosine.

EXAMPLE 6

This example illustrates the synthesis and chemical analysis of novel xanthine derivatives of the present invention as well as of those previously disclosed.

Alkylation of the N-7 position in xanthine derivatives to provide compounds 13, 17, 21, and 23 was carried out as described in Jacobson et al., *J. Med. Chem.*, 36, 2639–2644 (1993) and Daly et al., *J. Med. Chem.*, 29, 1305–1308 (1986). Compounds 8–12, 14, 18, 19, 20, and 25 were synthesized as described in Jacobson et al. (*Biochem. Pharmacol.*, 37, 3653–3661 (1988)); Shimada et al. (*J. Med. Chem.*, 35, 924–930 (1992)); and Shamim et al. (*J. Med. Chem.*, 32, 1231–1237 (1989)); compounds 7, 14, 18, and 19 have been disclosed in Müllet et al. (*J. Med. Chem.*, 36, 3341–3349 (1993)) and Shamin et al. (*J. Med. Chem.*, 35; 924–930 (1989)). Compounds 1–5 and 26, as well as 2-chloroadenosine, were purchased from Research Biochemicals International (Natick, Mass.). Compound 27 was disclosed in Thompson et al. (*J. Med. Chem.*, 34, 2877–2882 (1991)).

TABLE 1

| Compound | $R_1,R_3=$ | $R_7=$ | $R_8=$ | $K_i$, $\mu M(A_1)$ | $K_i$, $\mu M(A_2)$ | Conc. max. (nM) | % control | thresh (nM) | % control |
|---|---|---|---|---|---|---|---|---|---|
| 8-unsubstituted | | | | | | | | | |
| 1[a] | Me | H | H | 8.5 | 25 | 100 | 150 ± 30 | 1 | 130 ± 20 |
| 2 | Me | Me | H | 29 | 48 | 10 | 170 ± 20 | 1 | 120 ± 30 |
| 3[b] | Me,iBu[c] | H | H | 7 | 16 | >>10$^4$ | — | — | — |
| 8-cyclopentyl | | | | | | | | | |
| 4[d] | Me | H | cyclopentyl | 0.011 | 1.4 | >>10$^4$ | — | — | — |
| 5[e] | Pr | H | cyclopentyl | 0.00046 | 0.34 | 30 | 200 ± 10 | 1 | 130 ± 10 |
| 6 | Pr | Me | cyclopentyl | 2.3 | 11.4 ± 1.4 | 1000 | 180 ± 40 | 30 | 125 ± 30 |
| 7 | Pr,H[f] | H | cyclopentyl | 0.014 | 0.58 | 30 | 160 ± 40 | 1 | 130 ±20 |
| 8[g] | Pr | H | cyclopentyl | 0.00066 | 0.31 | >>10$^4$ | — | — | — |
| 9 | Pr | H | 3-fluorocyclopentyl | 0.042 | — | >>300 | — | — | — |
| 10 | Pr | H | 3-iodocyclopentyl | 0.058 | — | >>300 | — | — | — |
| 11 | Pr | H | cyclopenten-3-yl | 0.045 | 0.640 ± 0.061 | >>300 | — | — | — |
| 12 | Pr | H | noradamantyl | 0.0013 | 0.38 | 10 | 170 ± 20 | 1 | 120 ± 5 |
| 8-cyclohexyl | | | | | | | | | |
| 13 | Me | H | cyclohexyl | 0.030 ± 0.015 | 1.04 ± 0.20 | 3 | 160 ± 20 | 0.1 | 130 ± 20 |
| 14 | Me | Me | cyclohexyl | 28 | 17.1 | 3 | 150 ± 30 | 3 | 150 ± 30 |
| 15 | Me | Et | cyclohexyl | 6.66 ± 0.99 | 3.23 ± 0.36 | >>10$^4$ | — | — | — |
| 16 | Me | cyclopropylmethyl | cyclohexyl | 8.23 ± 1.62 | 4.53 ± 1.37 | >>10$^4$ | — | — | — |
| 17 | allyl | H | cyclohexyl | 0.0656 ± 0.0189 | 4.94 ± 0.68 | 10$^3$ | 260 ± 70 | 30 | 170 ± 40 |
| 18 | Pr | H | cyclohexyl | 0.0015 | 0.423 ± 0.055 | >>10$^4$ | — | — | — |
| 19 | Pr | Me | cyclohexyl | 2.7 | 9.24 ± 0.37 | 5 | 170 ± 50 | 5 | 170 ± 50 |
| 20 | Pr | H | cyclohexen-3-yl | 0.010 | 0.905 ± 0.128 | 10$^4$ | 150 ± 30 | 10$^4$ | 150 ± 30 |
| 21 | Me | H | cyclohexylmethyl | 0.610 ± 0.076 | 5.47 ± 0.86 | >>10$^4$ | — | — | — |
| 22 | Me | Me | cyclohexylmethyl | 3.71 ± 0.36 | 5.46 ± 0.47 | >>10$^4$ | — | — | — |
| 8-cycloheptyl | | | | | | | | | |
| 23 | Me | H | cycloheptyl | 0.0659 ± 0.0145 | 1.05 ± 0.19 | >>10$^4$ | — | — | — |
| 24 | Me | Me | cycloheptyl | 19.5 ± 2.5 | 3.27 ± 0.98 | >>10$^4$ | — | — | — |
| 8-styryl or 8-aryl | | | | | | | | | |
| 25[i] | Me | Me | 3-chlorostyryl | 28 | 0.054 | 30 | 160 ± 30 | 30 | 160 ± 30 |
| 26[j] | Pr | H | p-φ-OCH$_2$CONH(CH$_2$)$_2$NH$_2$ | 0.0012 | 0.08 | >>10$^4$ | — | — | — |

TABLE 1-continued

| Compound | $R_1,R_3=$ | $R_7=$ | $R_8=$ | $K_i$, $\mu M(A_1)$ | $K_i$, $\mu M(A_2)$ | Conc. max. (nM) | % control | thresh (nM) | % control |
|---|---|---|---|---|---|---|---|---|---|
| non-xanthine antagonist | | | | | | | | | |
| 27 | | | 9-ethyl-6-cyclopentyladenine | 0.44 | 17 | $>>10^4$ | — | — | — |

[a]theophylline; [b]IBMX; [c]1-methyl-3-isobutyl; [d]CPT; [e]CPX; [f]1-propyl-3-H-analogue (Müller et al., J.Med.Chem., 36, 3341–3349 (1992)); [g]2-thio instead of oxo; [h]KW-3902; [i]CSC; [j]XAC An alkyl or cycloalkyl carboxylic acid was reacted with 5,6-diamino-1,3-dimethyluracil to obtain the corresponding amide, including 5-(cycloheptanoylamino)-6-amino-1,3-methyluracil and 5-(cyclohexylmethylcarbonyl)-6-amino-1,3-methyluracil, using the following protocol:

The acid (1 equiv) was dissolved in a minimum volume of N,N-dimethylformamide (DMF) containing 1,3-dialkyl-5,6-diaminouracil (1.5 equiv). 1-(3-Dimethylamino-propyl)-3-ethyl carbodiimide:HCl (1 equiv) was added, followed by a catalytic amount (0.05 equiv) of 4-(N,N-dimethylamino)pyridine and 0.05 equiv of imidazole. The mixture was stirred at room temperature for 3 hours, and saturated sodium chloride solution was added (for 1,3-dipropyl derivatives, water was used here) to form a precipitate or amorphous insoluble fraction. The insoluble residue was filtered and dissolved in 4 N aqueous sodium hydroxide containing sufficient methanol to obtain a clear solution. The mixture was heated at 60° C. for 2 hours or until the complete disappearance of starting material, as judged using TLC (silica plate, $CHCl_3$; $CH_3OH$; HOAc; 85:10:5 v/v). The mixture was cooled and acidified to pH 1 with 6 N aqueous hydrochloric acid solution. The precipitate was washed with water, dried, and further purified using a preparative silica plate (85–95% $CHCl_3$; 5–15% methanol; 1–5% HOAC).

The new compounds were characterized (and resonances assigned) by 300 MHz proton nuclear magnetic resonance mass spectrometry using a Varian GEMINI-300 FT-NMR spectrometer. Unless noted, chemical shifts are expressed as ppm downfield from tetramethylsilane. New compounds were characterized by chemical ionization mass spectrometry ($NH_3$) on a mass spectrometer or in the EI mode using a VG707OF mass spectrometer. Representative spectral data for compounds 15, 16, 22, and 24 are: $^1H$ NMR $CDCl_3$ δ 3.42 (S, 3H $N_3CH_3$); 3.63 (S, 3H $N_5CH_3$); 3.89 (S, 6H $OCH_3$); 5.06 (S, 2H, $OCH_2$); 6.8 (S, 2H); 6.78 (d, 1H, J=16 Hz); 7.3–7.5 (m, 5H); 7.7 (D, 1H, J=16 Hz); MS (Cl) m/e 463 ($MH^+$ base), 375, 357.

Carbon, hydrogen, and nitrogen analyses were carried out by Atlantic Microlabs (Norcross, Ga.), and ±0.4% was acceptable. A summary of the characterization studies conducted pursuant to application of the aforementioned techniques is provided in Table 2, where the formulas and elemental analyses of compounds 15–17 and 21–24 are presented.

TABLE 2

| | | | | Calculated | | | Found | | |
|---|---|---|---|---|---|---|---|---|---|
| Compound | Yield % | M.p. (C.) | Formula | C | H | N | C | H | N |
| 15 | 81 | >170 | $C_{15}H_{22}N_4O_2 \cdot \frac{1}{4}H_2O$ | 61.10 | 7.69 | 19.00 | 61.25 | 7.48 | 18.59 |
| 16 | 91 | >120 | $C_{17}H_{24}N_4O_2 \cdot \frac{1}{4}H_2O$ | 63.63 | 7.70 | 17.46 | 63.62 | 7.57 | 17.16 |
| 17 | — | 126–128 | $C_{17}H_2N_4O_2 \cdot \frac{1}{2}H_2O$ | 63.38 | 7.08 | 17.28 | 63.14 | 7.17 | 17.32 |
| 21 | 74 | 236–238 | $C_{14}H_{20}N_4O_2$ | 60.85 | 7.30 | 20.27 | 60.77 | 7.32 | 20.22 |
| 22 | 73 | 158–159 | $C_{15}H_2N_4O_2 \cdot 0.15H_2O$ | 61.48 | 7.67 | 19.12 | 61.76 | 7.83 | 18.72 |
| 23 | 84 | 223–225 | $C_{14}H_{20}N_4O_2$ | 60.85 | 7.30 | 20.27 | 60.67 | 7.31 | 20.22 |
| 24 | 89 | 199–201 | $C_{15}H_2N_4O_2$ | 62.05 | 7.64 | 19.30 | 61.97 | 7.68 | 19.24 |

All xanthine derivatives were judged to be homogeneous using thin layer chromatography prior to biological testing.

EXAMPLE 7

This example describes the measurement of chloride efflux from CFPAC cells in response to contact between such cells and the xanthine derivatives of the present invention, including protocols required for culturing such cells and implementing such experimentation thereon.

CFPAC cells are pancreatic adenocarcinoma cells that are homozygous for the most common CFTR mutation, i.e., deletion of $Phe^{508}$ (Schoumacher et al., Proc. Natl. Acad. Sci., 87, 4012–4016 (1990)). CFPAC cells and CFTR-transfected CFPAC cells (CFPAC-4.7 CFTR) were obtained from R. Frizzell at the University of Alabama. The cells were split and seeded at low density on 24-well COSTAR plates in medium composed of Iscovels medium, supplemented with 10% (vol/vol) heat-inactivated fetal calf serum, 100 units/ml penicillin, 100 mg/ml streptomycin, 0.25 mg/ml fungizone, and 1% (wt/vol) glutamine, and adjusted to an osmolarity of 310 mOsm. All culture materials were obtained from Biofluids (Rockville, Md.). After 5 hours, the medium was replaced, and attached cells were allowed to grow to confluency during a period of 48–72 hours at 37° C. in an atmosphere of 5% $CO_2$/95% air.

Before each experiment, cells were loaded with [$^{36}Cl^-$] as follows. Confluent cells were washed four times in the medium disclosed in Example 6. Then, after aspirating the last wash, 500 μl of medium containing about $1.4 \times 10^8$ counts per minute (cpm) of [$^{36}Cl$]$^-$ (Amersham) were added to each well. The plates of cells were then incubated at 37° C. overnight in 5% $CO_2$/95% air, thus allowing [$^{36}Cl$]$^-$ isotopic equilibrium to be obtained. To initiate efflux experiments, concentrations of CPX and/or other xanthine derivatives were added to the cells, which were then incubated for 15 minutes at 19° C. After incubating, the cells were washed four times in successive aliquots of an ice-cold wash medium composed of 150 mM sodium-gluconate, 1.5 mM potassium gluconate, and 10 mM Na-Hepes (pH 7.4). At the end of the wash step, 500 µl of bicarbonate-free flux medium at 19° C. was added, and sampling was initiated by collecting 50 µl aliquots from each well at 0, 1, 2, 3, 5, 7, and 10 minutes. The flux medium consisted of 150 mM sodium gluconate, 1.5 mM potassium gluconate, 10 mM sodium Na-Hepes (pH 7.4), 100 µM bumetanide to inhibit efflux due to the cotransporter, and different concentrations of CPX or other drugs, e.g., $A_1$-adenosine antagonists and activators of cAMP synthesis, as required and described in subsequent examples. The osmolarity was 310 mOsm. At the end of each flux experiment, 20 µl of 50% trichloroacetic acid was added to a final concentration of 5% to obtain a measure of remaining radioactivity. Samples were mixed with 1.5 ml of Cytoscint fluid and assayed for two minutes on a Beckman LS9000 scintillation counter with windows at maximum width. Osmotic strength was measured by freezing point depression on an osmotic osmometer. See Eidelman et al., supra, 1992.

Table 1 summarizes the data derived from at least four repeats of the chloride efflux experiments using the xanthine derivatives of the present invention. Additionally, each data point within a repeated experiment was computed from the average of efflux measurements performed on four separate cells. The column labeled "Conc. max (nM)" presents the concentration of the xanthine derivative at its maximum impact upon chloride efflux, and the succeeding column to the right presents the percentage of chloride efflux at maximum impact relative to control. The column labeled "thresh (nM)" presents the minimum concentration of the xanthine derivative required to detect an effect upon chloride efflux, and the succeeding column to the right presents the percentage of chloride efflux at minimum detection relative to control. As can be seen in Table 1, the range of maximal stimulation is from about 3 nM (for compound 14, for example) to over $10^4$ nM (for compound 3, for example). Percentage increases over control at the maximum stimulation concentrations ranged from about 10% (i.e., non-effective compounds such as compounds 2 and 12) to about 260%±70% (for compound 17). The concentration of the xanthine derivative at threshold stimulation of the chloride efflux ranged from 0.1 nM (for compound 13, for example) to about $10^4$ nM (for compound 20, for example). Percentage increases over control at the threshold stimulation concentrations ranged from 120% (for compound 12) to about 170% (for compound 17, for example).

From these data, and in view of the preference of using a lesser concentration of any given drug to effect a desired result so as to minimize the incidence of undesired side effects, it is evident that compounds 6, 7, 13, 14, 17, 19, and 25 are preferred compounds in view of their noted ability to stimulate chloride efflux at µM or lesser concentrations.

Figure 12:
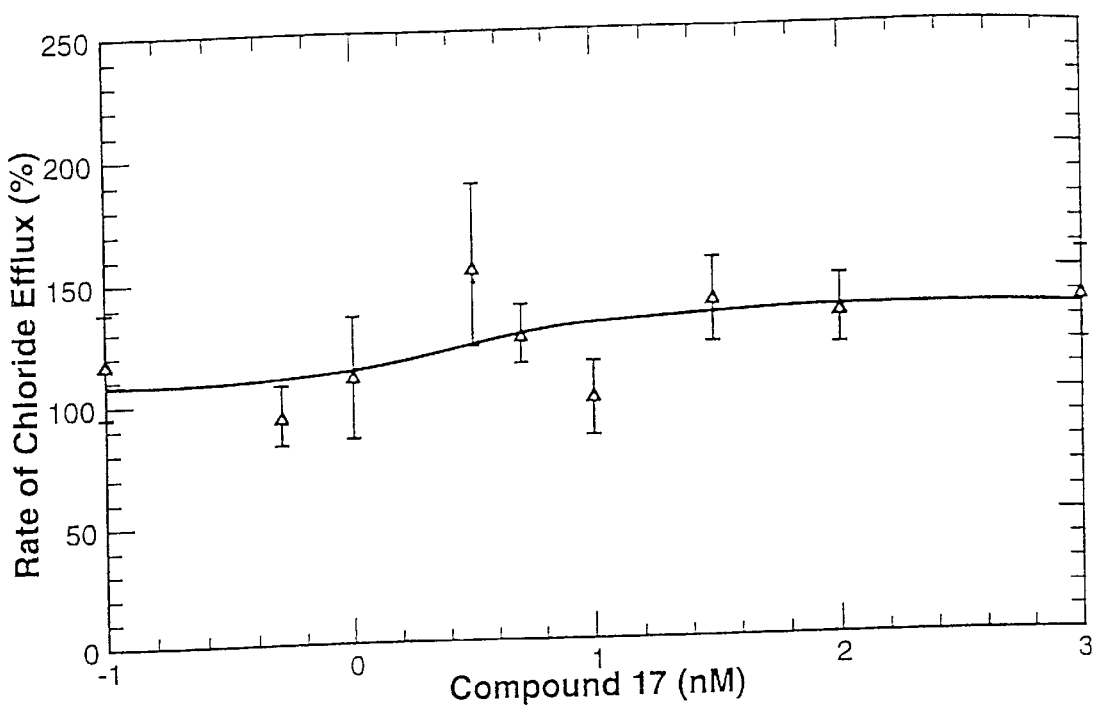
FIG. 12 depicts a graph of the results of $[^{36}Cl]^-$ efflux studies of CFPAC cells when placed in contact with compound 17 (1,3-diallyl-8-cyclohexylxanthine). The x-axis represents the nanomolar concentration of compound 17, and the y-axis represents the rate of chloride efflux as a percentage of control.

FIGS. 9–12 present flux study data that is presented graphically for compound 1, i.e., theophylline (FIG. 9); compound 5, i.e., CPX (FIG. 10); compound 22, i.e., 8-cyclohexylmethyl caffeine (FIG. 11); and compound 17, i.e., 1,3-diallyl-8-cyclohexylxanthine (FIG. 12). The vertical axis in each of the graphs of FIGS. 9–12 represents the rate of [$^{36}$Cl]$^-$ efflux (FA) of the radiolabeled chloride as a function of the concentration of the compound tested (horizontal axis). These were calculated by linear regression of the log (FA) as a function of time, using standard techniques, and are presented as a percentage relative to the rate constants of control wells on the same plate. Data were handled with a Quatro-Pro 4.0 program. The error bars represent the S.E.M. values of four experiments (i.e., n=4).

As can be seen by simple observation of FIGS. 9–12, each of compounds 1, 5, and 22 has the characteristic of inducing 200% of the efflux rate as compared to control. Compound 17 also demonstrates in excess of 100% of the efflux capability of the control, but to a lesser extent as compared to the other three compounds. Of the four compounds whose results are presented herein graphically, compounds 1 and 22 have little affinity for either tested adenosine receptor, compound 17 has moderate affinity for $A_1$ receptors ($K_i \cong 0.07$), and compound 5 has extreme affinity for $A_1$ receptors ($K_i \cong 0.0005$). Despite the fact that compound 17 has significantly less affinity for $A_1$-receptors than compound 5, for example, compound 17 has been shown to be significantly more efficacious in its absolute chloride efflux capability, as noted in Table 1 (a maximum of 260% of control for compound 17 versus 200% of control for compound 5).

EXAMPLE 8

This example illustrates assays for the detection of adenosine receptor binding and the results of such assays performed in partial characterization of the novel xanthine derivatives of the present invention.

Rat cerebral cortical membranes and striatal membranes were prepared according to the procedure of Hide et al., *Mol. Pharmacol.*, 41, 352–359 (1992) and treated with adenosine deaminase (2 U/ml) for 30 minutes at 37° C. prior to storage at −70° C. Solid samples of the adenosine derivatives were dissolved in dimethyl sulfoxide (DMSO) and stored in the art at −20° C. The stock solutions were diluted with DMSO to a concentration of <0.1 mM prior to addition to the aqueous medium. The final concentration of DMSO in the assay medium was generally 2%.

Inhibition of binding of 1 nM [$^3$H]$N^6$-phenylisopropyladenosine (Dupont NEN, Boston, Mass.) to $A_1$ receptors in rat cerebral cortex membranes was measured as described in Schwabe et al., *Naunyn-Schmiedeberg's Arch. Pharmacol.*, 313, 179–187 (1980), and Jacobson et al., *J. Med. Chem.*, 36, 1333–1342 (1993a). Membranes (~100 µg protein per tube) were incubated for 1.5 hours at 37° C. in a total volume of 0.5 ml of 50 mM tris hydrochloride at pH 7.4. Test drugs were dissolved in DMSO and added in 10 µl aliquots, resulting in a final DMSO concentration of 2%. Bound and free radioligand were separated by addition of 3 ml of a buffer containing 50 mM tris hydrochloride, at pH 7.4 at 5° C., followed by vacuum filtration using a Brandel Cell Harvester (Brandel, Gaithersburg, Md.) and a Whatman GF/B glass fiber filter with additional washes totaling 9 ml of buffer. Non-specific binding was determined with 10 µM 2-chloroadenosine.

Inhibition of binding of 5 nM [$^3$H]CGS 21680 (2-[4-[(2-carboxyethyl)-phenyl]ethylamino]-5'-N-ethylcarboxamidoadenosine) (Dupont NEN, Boston, Mass.) to $A_{2a}$ receptors was carried out as reported in Jarvis et al., *J. Pharmacol. Exp. Therap.*, 251, 888–893 (1989). Membranes (~80 µg protein per tube) were incubated for one hour at 25° C. in a total volume of 0.5 ml of a buffer solution consisting of 50 mM tris hydrochloride and 10 mM $MgCl_2$ at pH 7.4. Test drugs were dissolved in DMSO and added in 10 µl aliquots, resulting in a final DMSO concentration of 2%. Non-specific binding was defined using 20 µM 2-chloroadenosine. Filtration was carried out using a Brandel Cell Harvester, as above, using the tris·HCl/MgCl$_2$ buffer recited hereinabove as the washing buffer.

At least six different concentrations spanning three orders of magnitude, adjusted appropriately for the IC$_{50}$ of each compound, were used. IC$_{50}$ values, computer-generated using a non-linear regression formula on the GraphPAD program (Institute for Scientific Information), were converted to apparent K$_i$ values using K$_D$ values (Jacobson et al., supra, 1993a; Ukena et al., FEBS Letters, 209, 122–128 (1986)) of 1.0 and 14 nM for [$^3$H]PIA and [$^3$H]CGS 21680 binding, respectively, and the method of Cheng et al. (Biochem. Pharmacol., 22, 3099–3108 (1973)).

The results of the adenosine receptor binding studies are presented in Table 1 for all of the xanthine derivatives under the columns "K$_i$, μM (A$_1$)" and "K$_i$, μM (A$_2$)." Receptor antagonists having a high affinity for a particular receptor are characterized by having very low K$_i$ values, as determined using the assays described above for the A$_1$ and A$_2$ receptors. Accordingly, it can be seen that compound 5 has high affinity for the A$_1$ receptor whereas compound 6 has low affinity for either of the receptors tested.

Figure 13:
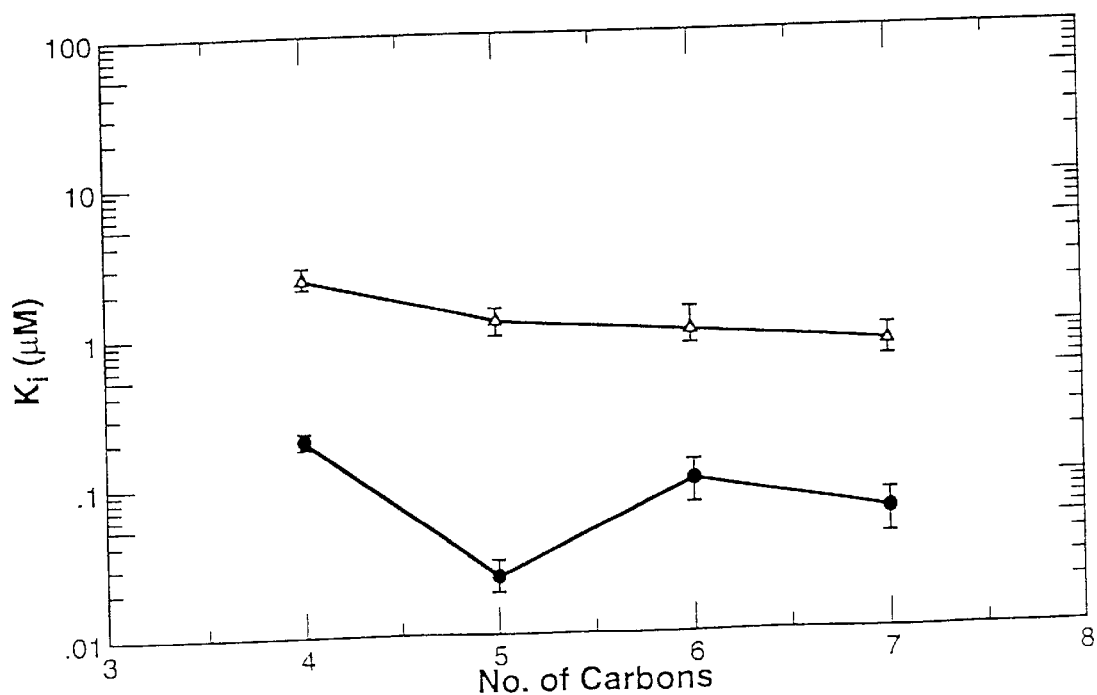
FIG. 13 depicts a graph of the result of chloride efflux studies where varying the size of the 8-cycloalkyl substituent (x-axis) of a theophylline derivative is tested for its impact on $K_i$ value (μM, y-axis). Data of the affinity of 8-cycloalkyltheophylline derivatives on rat cortical $A_1$-adenosine receptors (●) and rat striated $A_{2a}$-adenosine receptors (Δ) are shown.
Figure 14:
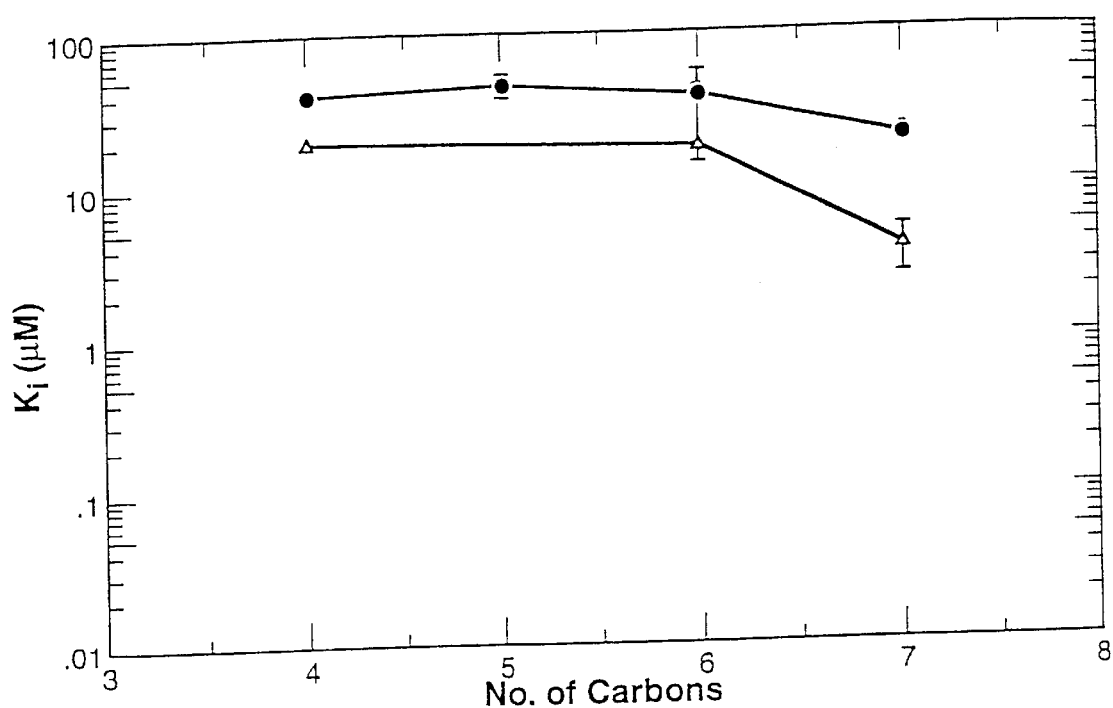
FIG. 14 depicts a graph of the result of chloride efflux studies where varying the size of the 8-cycloalkyl substituent (x-axis) of a caffeine derivative is tested for its impact on $K_i$ value (μM, y-axis). Data of the affinity of 8-cycloalkyl caffeine derivatives on rat cortical $A_1$-adenosine receptors (●) and rat striated $A_{2a}$-adenosine receptors (Δ) are shown.

FIGS. 13–14 also depict data derived from the receptor studies described above, with particular reference to ascertaining the effects of changing ring size of the 8-cycloalkyl substituent on binding at adenosine receptors. Values for rat cortical A$_1$-receptors (closed circles, ●) and rat striatal A$_{2a}$-receptors (open triangles, Δ) are incorporated into the graphs. The affinity of 8-cycloalkyltheophylline derivatives (FIG. 13) and the affinity of 8-cycloalkylcaffeine derivatives (FIG. 14) at A$_1$- and A$_2$-receptors are shown. Values are given as the average of two or three (±s.e.m.) determinations performed in triplicate. Data for 8-cyclobutyl derivatives are from Jacobson et al., J. Med. Chem., 36, 2639–2644 (1993b).

FIGS. 13 and 14 demonstrate that among derivatives of theophylline (1,3-dimethylxanthine), the cyclopentyl analogue, compound 4, had the highest A$_1$ affinity. Among derivatives of caffeine (1,3,7-trimethylxanthine), the cycloheptyl analogue, compound 24, showed some A$_{2a}$ affinity (6-fold), whereas smaller ring sizes (4–6) had little to no affinity (Jacobson et al., supra, 1993b). These structure activity relationships diverge greatly from those observed for the same compounds in stimulating Cl$^-$ efflux.

The results provided above, when considered in toto, indicate that compounds 6, 14, 17, and 19 provide the characteristics of substantial efflux activity at low concentration ranges coupled to a lack of activity at the adenosine receptors.

The results of these examples indicate that it is possible to (1) identify compounds that activate cellular chloride ion efflux using an in vitro liposome- and/or CFTR-binding assay; and (2) activate chloride efflux from CF cells by using a compound that has little or no affinity for the A$_1$- or the A$_2$-adenosine receptor, such as compounds 6, 14, 17, or 19. The most efficacious compound tested was compound 17. The therapeutic advantages of a drug that is able to activate chloride efflux from CF cells specifically without having an impact or substantial impact at adenosine receptors are appreciable, given that such drug action would be less encumbered by undesirable side effects to other tissues.

All of the references identified herein, including patents, patent applications, and publications, are hereby incorporated by reference in their entireties.

While the invention has been described with an emphasis upon preferred embodiments, it will be obvious to those of ordinary skill in the art that variations in the preferred method, compound, and composition can be used and that it is intended that the invention can be practiced otherwise than as specifically described herein. Accordingly, this invention includes all modifications encompassed within the spirit and scope of the invention as defined by the following claims.

What is claimed is:

1. A method of treating cystic fibrosis in a mammal comprising administering to said mammal a therapeutically effective amount of a compound having the formula

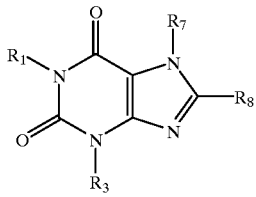

wherein $R_1$ and $R_3$ are the same and are $C_2$–$C_6$ alkenyl, $R_7$ is $C_1$–$C_6$ alkyl or hydrogen, and $R_8$ is $C_6$–$C_8$ cycloalkyl.

2. The method of claim 1, wherein $R_1$ and $R_3$ are allyl, $R_7$ is methyl or hydrogen, and $R_8$ is cyclohexyl.

3. The method of claim 1, wherein said mammal is a human.

4. The method of claim 3, wherein said compound is 1,3-diallyl-8-cyclohexylxanthine.

5. The method of claim 3, wherein said compound is administered to the lung of said human.

6. The method of claim 5, wherein said compound is administered as an aqueous pharmaceutical composition containing from about 0.001 to about 0.01% w/w of said compound.

7. A method of treating cystic fibrosis in a mammal comprising administering to said mammal a therapeutically effective amount of a compound having the formula

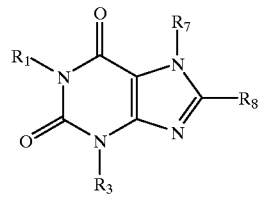

wherein (a) $R_1$ and $R_3$ are methyl, $R_7$ is cyclopropylmethyl, and $R_8$ is cyclohexyl; or (b) $R_1$ and $R_3$ are allyl, $R_7$ is hydrogen, and $R_8$ is cyclohexyl, cyclohexylmethyl, or cycloheptyl.

8. The method of claim 7, wherein said compound is 1,3-diallyl-8-cyclohexylxanthine.

9. The method of claim 7, wherein said mammal is a human.

10. The method of claim 9, wherein said compound is administered to the lung of said human.

11. The method of claim 10, wherein said compound is administered as an aqueous pharmaceutical composition containing about 0.001 to about 0.01% w/w of said compound.

* * * * *